(12) United States Patent
Bagga et al.

(10) Patent No.: US 11,338,061 B2
(45) Date of Patent: May 24, 2022

(54) DYNAMIC BIOACTIVE BONE GRAFT MATERIAL HAVING AN ENGINEERED POROSITY

(71) Applicant: Prosidyan, Inc., New Providence, NJ (US)

(72) Inventors: Charanpreet S. Bagga, Basking Ridge, NJ (US); Hyun W. Bae, Los Angeles, CA (US); Thomas E. Day, Rolla, MO (US)

(73) Assignee: Prosidyan, Inc., New Providence, NJ (US)

( * ) Notice: Subject to any disclaimer, the term of this patent is extended or adjusted under 35 U.S.C. 154(b) by 139 days.

(21) Appl. No.: 16/695,997

(22) Filed: Nov. 26, 2019

(65) Prior Publication Data
US 2020/0093963 A1    Mar. 26, 2020

Related U.S. Application Data

(62) Division of application No. 12/914,468, filed on Oct. 28, 2010, now abandoned.
(Continued)

(51) Int. Cl.
*A61F 2/28* (2006.01)
*A61L 27/10* (2006.01)
(Continued)

(52) U.S. Cl.
CPC ......... *A61L 27/427* (2013.01); *A61L 2400/12* (2013.01); *A61L 2430/02* (2013.01)

(58) Field of Classification Search
CPC ...... A61L 27/54; A61L 2430/02; A61L 27/56; A61L 27/58; A61L 2300/412;
(Continued)

(56) References Cited

U.S. PATENT DOCUMENTS 4,693,721 A   9/1987   Ducheyne
4,861,733 A   8/1989   White
(Continued)

FOREIGN PATENT DOCUMENTS

EP   1660146 A1   3/2005
EP   1729675 A2   9/2005
(Continued)

OTHER PUBLICATIONS

Extended European Search Report for corresponding EP Appl. No. 18167603.2 dated Jul. 4, 2018.
(Continued)

*Primary Examiner* — Ann Schillinger
(74) *Attorney, Agent, or Firm* — Farber LLC

(57) ABSTRACT

The present disclosure relates to a dynamic bioactive bone graft material having an engineered porosity. In one embodiment, a bone graft material is provided having bioactive glass fibers arranged in a porous matrix that is moldable into a desired shape for implantation. The material can be substantially without additives and can include at least one nanofiber. The porous matrix may include a combination of one or more pore sizes including nanopores, macropores, mesopores, and micropores. In another embodiment, a bone graft implant is provided having a matrix comprising a plurality of overlapping and interlocking bioactive glass fibers, and having a distributed porosity based on a range of pores provided in the bioactive glass fibers. The distributed porosity can comprise a combination of macropores, mesopores, and micropores, and the matrix can be formable into a desired shape for implantation into a patient.

20 Claims, 14 Drawing Sheets

Related U.S. Application Data

(60) Provisional application No. 61/389,964, filed on Oct. 5, 2010, provisional application No. 61/256,287, filed on Oct. 29, 2009.

(51) Int. Cl.
*A61L 27/12* (2006.01)
*A61L 27/54* (2006.01)
*A61L 27/56* (2006.01)
*A61L 27/58* (2006.01)
*A61L 27/42* (2006.01)

(58) Field of Classification Search
CPC .. A61L 27/10; A61L 27/365; A61L 2300/604; A61L 31/146; A61L 33/0029; A61L 33/0088; A61L 27/427; A61L 2400/12; A61F 2/28; A61F 2002/2835; A61F 2002/2817; A61F 2002/30014; A61F 2002/30016; A61F 2002/3092; A61F 2210/0004; A61F 2310/00329; A61F 2/2846; A61F 2002/30062
See application file for complete search history.

(56) References Cited

U.S. PATENT DOCUMENTS

| | | | |
|---|---|---|---|
| 5,030,233 | A | 7/1991 | Ducheyne |
| 5,429,996 | A | 7/1995 | Kaneko |
| 5,776,193 | A | 7/1998 | Kwan et al. |
| 6,054,400 | A | 4/2000 | Brink et al. |
| 6,139,585 | A | 10/2000 | Li |
| 6,398,814 | B1 | 6/2002 | Paasimaa |
| 6,482,444 | B1 | 11/2002 | Bellantone et al. |
| 6,517,857 | B2 | 2/2003 | Ylanen et al. |
| 6,783,712 | B2 | 8/2004 | Slivka et al. |
| 6,808,585 | B2 | 10/2004 | Boyce et al. |
| 6,902,584 | B2 | 6/2005 | Kwan et al. |
| 6,955,716 | B2 | 10/2005 | Xu |
| 7,018,460 | B2 | 3/2006 | Xu |
| 7,241,486 | B2 | 7/2007 | Pirhonen |
| 7,621,963 | B2 | 11/2009 | Simon et al. |
| 7,767,221 | B2 | 8/2010 | Lu et al. |
| 7,964,206 | B2 | 6/2011 | Suokas et al. |
| 8,093,166 | B2 | 1/2012 | Moimas et al. |
| 8,153,148 | B2 | 4/2012 | Maspero et al. |
| 8,163,030 | B2 | 4/2012 | Maspero et al. |
| 8,303,967 | B2 | 11/2012 | Clineff et al. |
| 8,889,178 | B2 | 11/2014 | Bagga et al. |
| 9,381,274 | B2 | 7/2016 | Bagga et al. |
| 2002/0160175 | A1 | 10/2002 | Pirhonen |
| 2004/0009598 | A1 | 1/2004 | Hench et al. |
| 2004/0078090 | A1* | 4/2004 | Binette ............ A61L 27/18 623/23.76 |
| 2004/0265385 | A1* | 12/2004 | West ............ A61L 27/42 424/484 |
| 2005/0090905 | A1 | 4/2005 | Hawkins et al. |
| 2005/0113938 | A1* | 5/2005 | Jamiolkowski ...... A61L 27/46 623/23.74 |
| 2005/0118236 | A1 | 6/2005 | Qiu et al. |
| 2005/0226904 | A1* | 10/2005 | Choi ............ A61L 27/56 424/426 |
| 2005/0249773 | A1 | 11/2005 | Maspero et al. |
| 2006/0067969 | A1 | 3/2006 | Lu et al. |
| 2006/0280775 | A1 | 6/2006 | Ashammakhi |
| 2007/0141110 | A1 | 2/2007 | Stone |
| 2007/0059379 | A1 | 3/2007 | Gerber |
| 2007/0141111 | A1 | 6/2007 | Suokas et al. |
| 2007/0142916 | A1 | 6/2007 | Olson, Jr. et al. |
| 2007/0240601 | A1 | 10/2007 | Chou et al. |
| 2008/0038534 | A1* | 2/2008 | Zenati ............ A61L 27/56 428/312.6 |
| 2008/0187571 | A1* | 8/2008 | Clineff ............ A61L 27/46 424/426 |
| 2008/0249638 | A1* | 10/2008 | Asgari ............ A61L 27/54 623/23.75 |
| 2009/0208428 | A1 | 8/2009 | Hill et al. |
| 2009/0276056 | A1* | 11/2009 | Bose ............ A61L 27/32 623/23.72 |
| 2010/0010513 | A1* | 1/2010 | Yun ............ C01G 25/02 606/151 |
| 2010/0136086 | A1* | 6/2010 | Day ............ A61L 27/56 424/426 |
| 2010/0179662 | A1 | 7/2010 | Verne et al. |
| 2011/0066242 | A1 | 3/2011 | Lu et al. |
| 2011/0081396 | A1* | 4/2011 | Denry ............ A61L 27/58 424/423 |
| 2011/0082564 | A1 | 4/2011 | Liu et al. |
| 2011/0106255 | A1 | 5/2011 | Liu et al. |
| 2011/0106272 | A1 | 5/2011 | Liu |
| 2011/0140316 | A1 | 6/2011 | Bagga et al. |
| 2011/0144763 | A1 | 6/2011 | Bagga et al. |
| 2011/0204537 | A1 | 8/2011 | Liu et al. |
| 2011/0206828 | A1 | 8/2011 | Liu et al. |
| 2011/0256203 | A1 | 10/2011 | Kim et al. |
| 2012/0164187 | A1 | 6/2012 | Ollila et al. |
| 2012/0203355 | A1 | 8/2012 | Liu |
| 2012/0219635 | A1 | 8/2012 | Liu |
| 2012/0265167 | A1 | 10/2012 | Simonson et al. |
| 2012/0276164 | A1 | 11/2012 | Tuomimen et al. |
| 2012/0288699 | A1 | 11/2012 | Ahlberg et al. |

FOREIGN PATENT DOCUMENTS

| | | |
|---|---|---|
| EP | 1733746 A2 | 6/2006 |
| EP | 2040765 A2 | 1/2008 |
| JP | 2002524152 A | 8/2002 |
| JP | 2004305748 A | 11/2004 |
| JP | 2009500054 A | 1/2009 |
| WO | 0076486 A1 | 12/2000 |
| WO | 200076486 A1 | 12/2000 |
| WO | 2004005533 A2 | 1/2004 |
| WO | 2004049904 A2 | 6/2004 |
| WO | 2005007802 A2 | 1/2005 |
| WO | 05018698 A1 | 3/2005 |
| WO | 05086706 A2 | 9/2005 |
| WO | 06118554 A1 | 11/2006 |
| WO | 2008049242 A1 | 11/2006 |
| WO | 2007144662 A1 | 12/2007 |
| WO | 08002682 A2 | 1/2008 |
| WO | 2009027594 A2 | 3/2009 |

OTHER PUBLICATIONS

Rejection Decision with English translation dated Oct. 30, 2015 issued in Chinese Patent Application No. 201080049374.2, pp. 1-18.
Author Unknown, Chinese Office Action dated Oct. 15, 2014, Chinese Application No. 201080049374.2, filed Oct. 28, 2010, (including English translation), pp. 1-11.
Jiashou Dong et al., "Medical Equipment and Management Thereof", Southwest Jiaotong University Press, 1st edition in Oct. 2006, published on Oct. 31, 2006, p. 150, lines 11-14.
Japanese Office Action dated Sep. 24, 2014, Japanese Application No. 2012-237071, filed Oct. 28, 2010, English translation only, pp. 1-3.
R. H. Mattila et al., "Fibre-reinforced composite implant: in vitro mechanical interlocking with bone model material and residual monomer analysis", Journal of Materials Science, vol. 41., No. 13, Jul. 2006, pp. 4321-4326.
Jing Yi et al., "Sol-gel derived mesoporous bioactive glass fibers as tissue-engineering scaffolds", Journal of Sol-Gel Science and Technology, vol. 45, No. 1, Jan. 2008, pp. 115-119.
Sari Tuusa et al., "A Review of Two Animal Studies Dealing with Biological Responses to Glass-Fibre-Reinforced Composite Implants in Critical Size Calvarial Bone Defects in Rabbits", Key Engineering Materials, vols. 361-313, 2008, pp. 471-474.
Mervi Puska et al., "Biomineralization of Glass Fibre Reinforced Porous Acrylic Bone Cement", Key Engineering Materials, vols. 330-332, 2007, pp. 815-818.

(56) References Cited

OTHER PUBLICATIONS

Extended European Search Report for corresponding European Appl. No. 10827483.8 dated Apr. 22, 2014.
Wei, Xia, et al., "Fabrication and in vitro biomineralization of bioactive glass (BG) nanofibres", Nanotechnology, IOP, vol. 18, No. 13, Apr. 4, 2007, p. 135601.
Woo, et al., "Comparative Evaluation of Nanofibrous Scaffolding for Bone Regeneration in Critical-Size Calvarial Defects", Tissue Engineering: Part A, vol. 15, No. 8, 2009, pp. 2155-2162.

* cited by examiner

3 Days

1 Day

3 Days

3 Days

4 Days

2 Days

6 Days

DYNAMIC BIOACTIVE BONE GRAFT MATERIAL HAVING AN ENGINEERED POROSITY

CROSS-REFERENCE TO RELATED APPLICATIONS

This application is a divisional of U.S. patent application Ser. No. 12/914,468 filed Oct. 28, 2010, which application claims priority to U.S. Provisional Patent Application No. 61/389,964, filed Oct. 5, 2010, and entitled "DYNAMIC BIOACTIVE BONE GRAFT MATERIAL AND METHOD OF USE," and to U.S. Provisional Patent Application No. 61/256,287, filed Oct. 29, 2009, and entitled "BONE GRAFT MATERIAL," both of which are herein incorporated by reference in their entirety.

FIELD

The present disclosure relates generally to bone graft materials and methods of using such materials. More particularly, the present disclosure relates to a dynamic bioactive synthetic bone graft material having an engineered porosity, and implants formed from such materials and their use.

BACKGROUND

There has been a continuing need for improved bone graft materials. Known autograft materials have acceptable physical and biological properties and exhibit the appropriate structure for bone growth. However, the use of autogenous bone requires the patient to undergo multiple or extended surgeries, consequently increasing the time the patient is under anesthesia, and leading to considerable pain, increased risk of infection and other complications, and morbidity at the donor site.

Alternatively, allograft devices may be used for bone grafts. Allograft devices are processed from donor bone. Allograft devices may have appropriate structure with the added benefit of decreased risk and pain to the patient, but likewise incur the increased risk arising from the potential for disease transmission and rejection. Autograft and allograft devices are further restricted in terms of variations on shape and size.

Unfortunately, the quality of autograft and allograft devices is inherently variable, because such devices are made from harvested natural materials. Likewise, autograft supplies are also limited by how much bone may be safely extracted from the patient, and this amount may be severely limited in the case of the seriously ill or weak.

A large variety of synthetic bone graft materials are currently available for use. Recently, new materials, such as bioactive glass ("BAG") particulate-based materials, have become an increasingly viable alternative or supplement to natural bone-derived graft materials. These new (non-bone derived) materials have the advantage of avoiding painful and inherently risky harvesting procedures on patients. Also, the use of non-bone derived materials can reduce the risk of disease transmission. Like autograft and allograft materials, these new artificial materials can serve as osteoconductive scaffolds that promote bone regrowth. Preferably, the graft material is resorbable and is eventually replaced with new bone tissue.

Many artificial bone grafts available today comprise materials that have properties similar to natural bone, such as compositions containing calcium phosphates. Exemplary calcium phosphate compositions contain type-B carbonated hydroxyapatite $(Ca_5(PO_4)_{3x}(CO_3)_x(OH))$. Calcium phosphate ceramics have been fabricated and implanted in mammals in various forms including, but not limited to, shaped bodies and cements. Different stoichiometric compositions, such as hydroxyapatite (HA), tricalcium phosphate (TCP), tetracalcium phosphate (TTCP), and other calcium phosphate (CaP) salts and minerals have all been employed in attempts to match the adaptability, biocompatibility, structure, and strength of natural bone. Although calcium phosphate based materials are widely accepted, they lack the ease of handling, flexibility and capacity to serve as a liquid carrier/storage media necessary to be used in a wide array of clinical applications. Calcium phosphate materials are inherently rigid, and to facilitate handling are generally provided as part of an admixture with a carrier material; such admixtures typically have an active calcium phosphate ingredient to carrier ratio of about 50:50, and may have as low as 10:90.

The roles of porosity, pore size and pore size distribution in promoting revascularization, healing, and remodeling of bone have been recognized as important contributing factors for successful bone grafting materials. However, currently available bone graft materials still lack the requisite chemical and physical properties necessary for an ideal graft material. For instance, currently available graft materials tend to resorb too quickly, while some take too long to resorb due to the material's chemical composition and structure. For example, certain materials made from hydroxyapatite tend to take too long to resorb, while materials made from calcium sulphate or B-TCP tend to resorb too quickly. Further, if the porosity of the material is too high (e.g., around 90%), there may not be enough base material left after resorption has taken place to support osteoconduction. Conversely, if the porosity of the material is too low (e.g., 30%) then too much material must be resorbed, leading to longer resorption rates. In addition, the excess material means there may not be enough room left in the residual graft material for cell infiltration. Other times, the graft materials may be too soft, such that any kind of physical pressure exerted on them during clinical usage causes them to lose the fluids retained by them.

Thus, there remains a need for improved bone graft materials that provide the necessary biomaterial, structure and clinical handling necessary for optimal bone grafting. What is also needed are dynamic bone graft materials that provide an improved mechanism of action for bone grafting, by allowing the new tissue formation to be achieved through a physiologic process rather than merely from templating. There likewise remains a need for an artificial bone graft material that can be manufactured as required to possess varying levels of porosity, such as nano, micro, meso, and macro porosity. Further, a need remains for a bone graft material that can be selectively composed and structured to have differential or staged resorption capacity, while providing material than can be easily molded or shaped into clinically relevant shapes as needed for different surgical and anatomical applications. In particular, it would be highly desirable to provide a bone graft material that includes the characteristics of variable degrees of porosity, differential bioresorbability, compression resistance and radiopacity, and also maximizes the content of active ingredient relative to carrier materials such as collagen. Even more desirable would be a bone graft material that possesses all of the advantages mentioned above, and includes antimicrobial properties as well as allowing for drug delivery that can be easily handled in clinical settings. Embodiments of the present disclosure address these and other needs.

SUMMARY

The present disclosure provides bioactive bone graft materials having an engineered porosity and implants formed from such materials and their use. These graft materials are dynamic and accordingly can be molded and shaped as desired. These bone graft materials address the unmet needs aforementioned by providing the necessary biomaterial, structure and clinical handling for optimal bone grafting. In addition, these bone graft materials provide an improved mechanism of action for bone grafting, by allowing the new tissue formation to be achieved through a physiologic process of induction and formation rather than merely from templating and replacement. Further, these artificial bone graft materials can be manufactured as required to possess varying levels of porosity, such as nano, micro, meso, and macro porosity. The bone graft materials can be selectively composed and structured to have differential or staged resorption capacity, while being easily molded or shaped into clinically relevant shapes as needed for different surgical and anatomical applications. Additionally, these bone graft materials may have variable degrees of porosity, differential bioresorbability, compression resistance and radiopacity, and can also maximize the content of active ingredient relative to carrier materials such as collagen. These bone graft materials also possess antimicrobial properties as well as allows for drug delivery. The materials can also be easily handled in clinical settings.

In one embodiment, a bone graft material is provided having bioactive glass fibers arranged in a porous matrix. The material can be substantially without additives and can include at least one nanofiber. The porous matrix may include a combination of one or more pore sizes including nanopores, macropores, mesopores, and micropores.

In another embodiment, a bone graft implant is provided having a matrix comprising a plurality of overlapping and interlocking bioactive glass fibers, and having a distributed porosity based on a range of pores provided in the bioactive glass fibers. The distributed porosity can comprise a combination of macropores, mesopores, and micropores, and the matrix can be formable into a desired shape for implantation into a patient. The distributed porosity can comprise nanopores.

In yet another embodiment, a bone graft implant comprising a flexible matrix of bioactive glass fibers is provided. The matrix is dynamic and allows movement of the fibers with respect to one another. Furthermore, the matrix has a structure similar to a natural fibrin clot. Also provided is a dynamic bone graft implant comprising a flexible matrix of bioactive glass fibers. The fibers of the flexible matrix are movable with respect to one another when under a physiologic pressure that is being exerted during a natural healing process.

In still another embodiment, a method of treating a bone defect is provided. The method comprises identifying a bone defect to be treated. The bone defect may be one residing in a human patient. The next step includes providing a bone graft material comprising a porous, fibrous matrix of bioactive glass fibers, wherein the fibers are characterized by fiber diameters ranging from about 5 nanometers to about 100 micrometers, and wherein the porosity of the matrix ranges from about 100 nanometers to about 1 millimeter. The bone graft material is formed into an implant that is then introduced to the bone defect, and osteogenic activity is allowed to occur at the bone defect to facilitate bone repair.

Prior to introducing the bone graft material, the material may be molded or shaped, such as by filling a mold tray with the material. If desired, the material may be compressed into the mold tray. Fluid may be added to the material prior to introduction into the mold tray. The fluid may be a saline, or it may be a naturally occurring body fluid such as blood. The bone graft material may be differentially activated. For example, the porous, fibrous matrix may comprise a combination of bioresorbable subcomponents having different resorption rates. The subcomponents may include fibers or particulates, or a combination of both. In one embodiment, the matrix may include more than one type of fiber, and each fiber may have a different resorption rate. The faster resorbing fiber may be allowed to resorb after the step of introduction, and induce strong initial bone growth. The remaining matrix may be designed to stay in the site for an extended period of time to allow for slower growth over time.

The bone graft material may be injected into the defect, or it may be plastered over the defect. In addition, the material may be plugged into the defect.

BRIEF DESCRIPTION OF THE DRAWINGS

The foregoing and other features of the present disclosure will become apparent to one skilled in the art to which the present disclosure relates upon consideration of the following description of exemplary embodiments with reference to the accompanying drawings. In the Figures.

DETAILED DESCRIPTION OF THE EMBODIMENTS

Figure 1A:
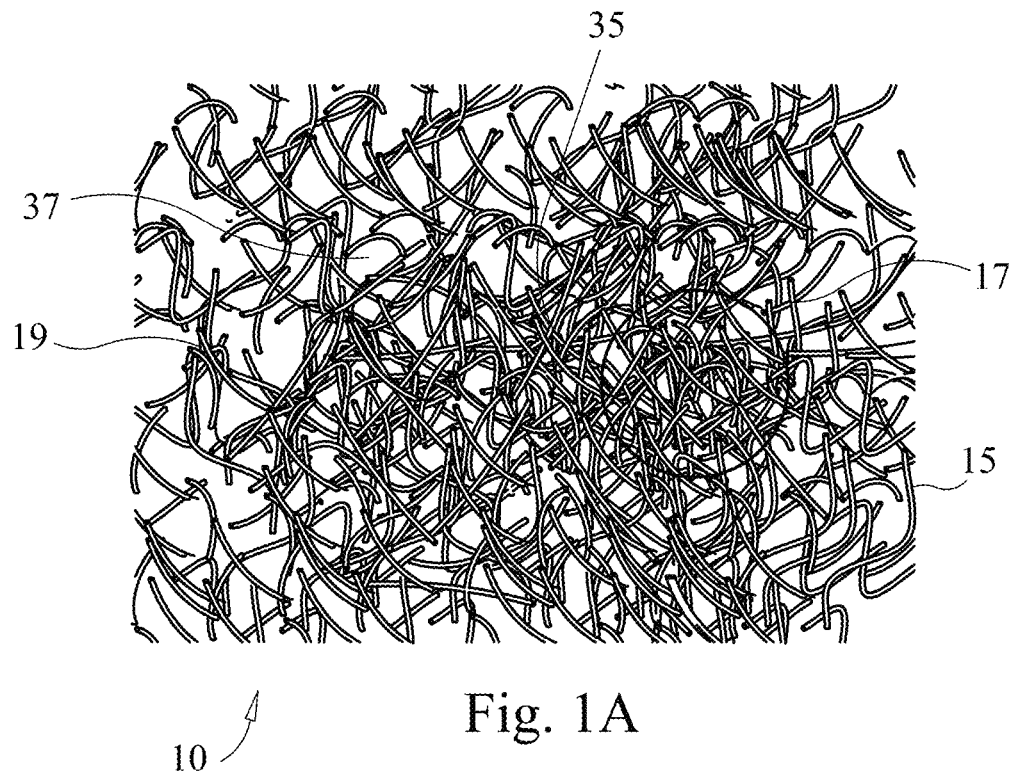
FIG. 1A is an illustration of a dynamic fibrous bioactive glass matrix according to a first embodiment of the present disclosure.

The standard method for healing natural tissue with synthetic materials has been to provide a device having the microstructure and macrostructure of the desired end product. Where the desired end product is cancellous bone, traditional bone grafts have been engineered to mimic the architecture of cancellous bone. Although this has been the current standard for bone grafts, it does not take into account the fact that bone is a living tissue. Each bony trabeculae is constantly undergoing active biologic remodeling in response to load, stress and/or damage. In addition, cancellous and cortical bone can support a vast network of vasculature. This network not only delivers nutrients to sustain the living environment surrounding bone, but also supports red blood cells and marrow required for basic biologic function. Therefore, merely providing a synthetic material with the same architecture that is non-biologic is insufficient for optimal bone healing and bone health. Instead, what is required is a mechanism that can recreate the living structure of bone.

Traditional synthetics act as a cast, or template, for normal bone tissue to organize and form. Since these synthetics are not naturally occurring, eventually the casts or templates have to be resorbed to allow for normal bone to be developed. If these architectured synthetics do not resorb and do not allow proper bone healing, they simply become foreign bodies that are not only obstacles, but potentially detrimental, to bone healing. This phenomenon has been observed in many studies with slow resorbing or non-resorbing synthetics. Since these synthetics are just inert, non-biologic structures that only resemble bone, they behave as a mechanical block to normal bone healing and development.

With the understanding that bone is a living biologic tissue and that inert structures will only impede bone healing, a different physiologic approach is presented with the present invention. Healing is a phasic process starting with some initial reaction. Each phase builds on the reaction that occurred in the prior phase. Only after a cascade of phases does the final development of the end product occur—bone. The traditional method has been to replace or somehow stimulate healing by placing an inert final product as a catalyst to the healing process. This premature act certainly does not account for the physiologic process of bone development and healing.

The physiologic process of bone healing can be broken down to three phases: (a) inflammation; (b) osteogenesis; and (c) remodeling. Inflammation is the first reaction to injury and a natural catalyst by providing the chemotactic factors that will initiate the healing process. Osteogenesis is the next phase where osteoblasts respond and start creating osteoid, the basic material of bone. Remodeling is the final phase in which osteoclasts and osteocytes then recreate the three-dimensional architecture of bone.

In a normal tissue repair process, at the initial phase a fibrin clot is made that provides a fibrous architecture for cells to adhere. This is the cornerstone of all connective tissue healing. It is this fibrous architecture that allows for direct cell attachment and connectivity between cells. Ultimately, the goal is to stimulate cell proliferation and osteogenesis in the early healing phase and then allow for physiologic remodeling to take place. Since the desired end product is a living tissue and not an inert scaffold, the primary objective is to stimulate as much living bone as possible by enhancing the natural fiber network involved in initiation and osteogenesis.

The bone graft material of the present disclosure attempts to recapitulate the normal physiologic healing process by presenting the fibrous structure of the fibrin clot. Since this bioactive material made of fibers is both osteoconductive as well as osteostimulative, this fibrous network will further enhance and accelerate bone induction. Further, the dynamic nature of the bioactive fibrous matrix or scaffold allows for natural initiation and stimulation of bone formation rather than placing a non-biologic template that may impede final formation as with current graft materials. The fibers of the present material can also be engineered to provide a chemical reaction known to selectively stimulate osteoblast proliferation or other cellular phenotypes.

The present disclosure provides bone graft materials and bone graft implants formed from these materials. These bone graft materials provide the necessary biomaterial, structure and clinical handling for optimal bone grafting. In addition, these bone graft materials provide an improved mechanism of action for bone grafting, by allowing the new tissue formation to be achieved through a physiologic process rather than merely from templating. Further, these artificial bone graft materials can be manufactured as required to possess varying levels of porosity, such as nano, micro, meso, and macro porosity. The bone graft materials can be selectively composed and structured to have differential or staged resorption capacity, while being easily molded or shaped into clinically relevant shapes as needed for different surgical and anatomical applications. Additionally, these bone graft materials may have variable degrees of porosity, differential bioresorbability, compression resistance and radiopacity, and can also maximize the content of active ingredient relative to carrier materials such as collagen. These bone graft materials also possess antimicrobial properties as well as allows for drug delivery. The materials can also be easily handled in clinical settings.

Embodiments of the present disclosure may employ a dynamic, ultraporous bone graft material, for example, having nano, micro, meso and macro porosities. The bone graft material can comprise bioactive ("BAG") fibers or a combination of BAG fibers and particulates of materials. Due to the size and length of the fibers, the bone graft material is a dynamic structure that can be molded or packed into a desired shape, while maintaining its porous structure. The bone graft material may be osteoconductive and/or osteostimulatory. By varying the diameter and chemical composition of the components used in the embodiments, the bone graft material may have differential activation (i.e., resorbability), which may facilitate advanced functions like drug delivery including antibiotics. Furthermore, the fibrous nature of the bone graft allows for stimulation and induction of the natural biologic healing process required for bone formation.

The embodiments of the bone graft material can include BAG fibers having a relatively small diameter, and in particular, a diameter less than 100 nanometers. In one embodiment, the fiber diameter can be less than 10 nanometers, and in another embodiment, the fiber diameter can be in the range of about 5 nanometers. Since the materials used in the embodiments are bioactive materials, the bone graft material may form a CaP layer on its surface when it interacts with body fluids.

In other embodiments, the bone graft material may comprise particulates in combination with fibers. The presence of particulate matter may be employed to modify or control the resorption rate and resorption profile of the bone graft material as well as provide mechanical strength and compression resistance. The particulate may be bioactive glass, calcium sulphate, calcium phosphate or hydroxyapatite. The particulate may be solid, or it may be porous.

The bone graft material may be moldable and can be packaged in functional molds for convenient clinical handling. In addition, the bone graft material can be mixed with other additives like collagen, etc., for example, to further facilitate handling. The bone graft material and collagen composite may be in the form of a foam, and the foam may additionally be shaped into a strip, a continuous rolled sheet, a sponge or a plug. However, it is understood that the foam may take any configuration with any variety of shapes and sizes. In addition, the bone graft material and collagen composite may take the form of a putty or other moldable material. For example, in one embodiment, the BAG fibers and particulates may be mixed with a slurry of collagen, poured into a mold of a desired shape, and frozen to yield a desire foam shape. In another example depending upon the type of collaged used, the foam can have a fixed shape or the foam may be turned into a putty with the addition of fluids such as saline, blood or bone marrow aspirate. Alternatively, the bone graft material may be in the form of an injectable material.

Putties can be made by combining the bone graft material with other additives such as CMC, hyaluronic acid, or sodium alginate, for instance. The ability to provide a bone graft material in the form of a putty renders the material easily usable, since the putty may be applied directly to the injury site by either injection or by plastering. Also, the ease of handling and moldability of the putty composition allows the clinician to form the material easily and quickly into any desired shape.

Reference will now be made to the embodiments illustrated in the drawings. It will nevertheless be understood that no limitation of the scope of the present disclosure is thereby intended, with such alterations and further modifications in the illustrated device and such further applications of the principles of the present disclosure as illustrated therein being contemplated as would normally occur to one skilled in the art to which the present disclosure relates.

The present disclosure relates to a synthetic bone graft material that can be manufactured in a wide variety of compositional and structural forms for the purpose of introducing a biocompatible, bioabsorbable structural matrix in the form of an implant for the repair or treatment of bone. The bone graft material can be an osteostimulative and/or osteoconductive implant having differential bioabsorbability. In some embodiments, the bone graft material may be substantially comprised of BAG fibers.

In one embodiment, the bone graft material can be selectively determined by controlling compositional and manufacturing variables, such as bioactive glass fiber diameter, size, shape, and surface characteristics as well as the amount of bioactive glass particulate content and structural characteristics, and the inclusion of additional additives, such as, for example tricalcium phosphate, hydroxyapatite, and the like. By selectively controlling such manufacturing variables, it is possible to provide an artificial bone graft material having selectable degrees of characteristics such as porosity, bioabsorbability, tissue and/or cell penetration, calcium bioavailability, flexibility, strength, compressibility and the like. These and other characteristics of the disclosed bone graft material are discussed in greater detail below.

The bioactive glass used in the bone graft material may have a composition similar to 45S5 (46.1 mol % $SiO_2$, 26.9 mol % CaO, 24.4 mol % $Na_2O$ and 2.5 mol % $P_2O_5$), 58S (60 mol % $SiO_2$, 36 mol % CaO and 4 mol % $P_2O_5$), S70C30 (70 mol % $SiO_2$, 30 mol % CaO), and the like. Of course, bioactive glasses that are silicon free may also be employed. For example, bioactive glass compositions that are $SiO_2$ free, and having boron instead of silicon, may also be used. The bone graft material may be tailored to have specific desired characteristics, such as increased X-ray opacity (for example, by incorporating strontium), slower or faster dissolution rate in vivo, surface texturing, or the like.

The bone graft material may serve as a scaffold for bone activity in the bone defect. The scaffolding materials used in the bone graft may be bioactive glasses, such as 45S5 glass, which can be both osteoconductive and osteostimulatory. As determined by applicants, the bioactive glass may have naturally inherent antimicrobial properties due to the presence of sodium in the material's composition. The extensive surface area provided by the present fibrous bone graft material allows for antimicrobial benefits with the use of this material.

Bone graft materials of the present disclosure can be flexible, moldable, or can be preformed to mimic, augment or replace specific shaped structures. For example, the bone graft materials can be formed into acetabulum cups and other skeletal modeled components employed in surgical procedures. The bone graft materials can be formed into any clinically useful shape, such as strips, blocks, wedges, and the like. The shapes may be formed by molding, as will be described in greater detail below, or simply by cutting, tearing, folding, or separating the fibrous material into the desired configuration for its clinical application In the embodiments, the bone graft material is formed from bioactive glass fibers, which may be manufactured having predetermined cross-sectional diameters sized as desired. The fibers may be formed by electro-spinning or laser spinning, for instance, to create consistently uniform fibers. In one embodiment, the bone graft material may be formed from a scaffold of fibers of uniform diameters. Further, the bioactive glass fibers may be formed having varying diameters and/or cross-sectional shapes, and may even be drawn as hollow tubes. Additionally, the fibers may be meshed, woven, intertangled and the like for provision into a wide variety of shapes.

For example, a bioactive glass fiber bone graft material manufactured such that each fiber is juxtaposed or out of alignment with the other fibers could result in a bone graft material having a glass-wool or "cotton-ball" appearance due to the large amount of empty space created by the random relationship of the individual glass fibers within the material. Such a manufacture enables a bone graft material with an overall soft or pliable texture so as to permit the surgeon to manually form the material into any desired overall shape to meet the surgical or anatomical requirements of a specific patient's surgical procedure. Such material also easily lends itself to incorporating additives randomly dispersed throughout the overall bone graft material, such as included bioactive glass particles, antimicrobial fibers, particulate medicines, trace elements or metals such as copper, which is a highly angiogenic metal, strontium, magnesium, zinc, etc. mineralogical calcium sources, and the like. Further, the bioactive glass fibers may also be coated with organic acids (such as formic acid, hyaluronic acid, or the like), mineralogical calcium sources (such as tricalcium phosphate, hydroxyapatite, calcium sulfate, or the like), antimicrobials, antivirals, vitamins, x-ray opacifiers, or other such materials.

The bone graft material may be engineered with fibers having varying resorption rates. The resorption rate of a fiber is determined or controlled by its material composition and by its diameter. The material composition may result in a slow reacting vs. faster reacting product. Similarly, smaller diameter fibers can resorb faster than larger diameter fibers. Also, the overall porosity of the material can affect resorption rate. Materials possessing a higher porosity mean there is less material for cells to remove. Conversely, materials possessing a lower porosity mean cells have to do more work, and resorption is slower. Accordingly, the bone graft material may contain fibers that have the appropriate material composition as well as diameter for optimal performance. A combination of different fibers may be included in the material in order to achieve the desired result.

As with the bioactive glass fibers, the inclusion of bioactive glass particles can be accomplished using particles having a wide range of sizes or configurations to include roughened surfaces, very large surface areas, and the like. For example, particles may be tailored to include interior lumens with perforations to permit exposure of the surface of the particles interior. Such particles would be more quickly absorbed, allowing a tailored material characterized by differential resorbability. The perforated or porous particles could be characterized by uniform diameters or uniform perforation sizes, for example. The porosity provided by the particles may be viewed as a secondary range of porosity accorded the bone graft material or the implant formed from the bone graft material. By varying the size, transverse diameter, surface texture, and configurations of the bioactive glass fibers and particles, if included, the manufacturer has the ability to provide a bioactive glass bone graft material with selectively variable characteristics that can greatly affect the function of the material before and after it is implanted in a patient. The nano and macro sized pores provide superb fluid soak and hold capacity, which enhances the bioactivity and accordingly the repair process.

Figure 1B:
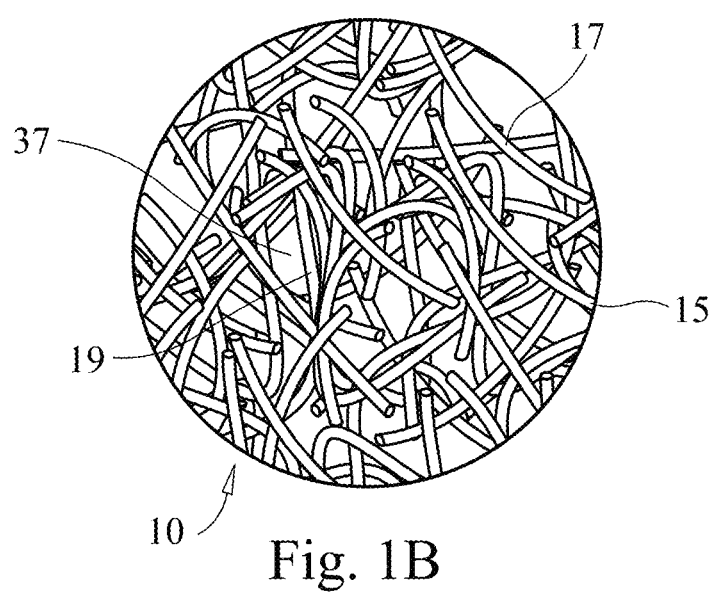
FIG. 1B is an enlarged view of the matrix of FIG. 1A.

FIGS. 1A and 1B illustrate a first embodiment bioactive fibrous scaffold 10 according to the present disclosure. The scaffold 10 is made up of a plurality of interlocking fibers 15 defining a three-dimensional porous support scaffold or matrix 10. The support matrix 10 is made up of bioactive glass fibers 15 that are interlocked or interwoven, not necessarily fused at their intersections 17. At least some of the fibers 15 may thus move over one another with some degree of freedom, yielding a support web 10 that is dynamic in nature. The composition of the fibers 15 used as the struts 19 of the resulting dynamic fibrous scaffold 10 are typically bioactive glass, ceramic or glass-ceramic formulations, such that within the range of fiber diameter and construct size, that the scaffolding fibers 15 are generally characterized as having the attributes of bioactivity.

The diameters of the fibers 15 defining the dynamic scaffold 10 are typically sufficiently small to allow for inherent interlocking of the resulting three-dimensional scaffold 10 upon itself, without the need for sintering, fusing or otherwise attaching the fibers 15 at their intersections 17, although some such fusing or attachment may be employed to further stiffen the scaffold 10 if desired. Hence the scaffold 10 is self constrained to not completely fall apart, yet the individual fibers 15 defining the support struts 19 are free to move small distances over each other to grant the scaffold 10 its dynamic qualities such that it remains flexible while offering sufficient support for tissue formation and growth thereupon. In addition, the availability of nano sized fibers can significantly enhance the surface area available for cell attachment and reactivity.

As will be described in detail below, pluralities of fibers 15 characterized as substantially having diameters below 1 micrometer (1000 nanometers) are sufficient to form dynamic scaffolding 10, as are pluralities of fibers 15 characterized as substantially having diameters below 100 nanometers. The scaffolding 10 may also be constructed from a plurality of fibers 15 having multi-modal diameter distributions, wherein combinations of diameters may be employed to yield specific combinations of dynamic flexibility, structural support, internal void size, void distribution, compressibility, dissolution and resorption rates, and the like. For example, some of the fibers 15 may be fast reacting and resorb quickly into bone to induce initial bone growth. In addition, some remnant materials of the bone graft material, such as other fibers 15 or particulates, may be designed to resorb over a more extended time and continue to support bone growth after the previously resorbed material has gone. This type of layered or staged resorption can be critically important in cases where the surgical site has not sufficiently healed after the first burst of bone growth activity. By providing varying levels of resorption to occur, the material allows greater control over the healing process and avoids the "all or none" situation.

Typically, the ranges of fiber diameters within a construct range starting from the nano level, where a nano fiber is defined as a fiber with a diameter less than 1 micron (submicron), up to about 100 microns; more typically, fiber diameters range from about 0.005 microns to about 10 microns; still more typically, fiber diameters range from about 0.05 to about 6 microns; yet more typically, fiber diameters range from 0.5 to about 20 microns; still more typically, fiber diameters range from about 1 micron to about 6 microns. In all cases, predetermined amounts of larger fibers may be added to vary one or more of the properties of the resultant scaffolding 10 as desired. It should be noted that as the amount of smaller (typically less than 10 micrometer) diameter fibers 15 decreases and more of the scaffolding construct 10 contains fibers 15 of relatively greater diameters, the entire construct 10 typically tends to become less self constrained. Thus, by varying the relative diameters and aspect ratios of constituent fibers 15 the resulting scaffold structure 10 may be tailored to have more or less flexibility and less or more load-bearing rigidity. Furthermore, fibers 15 may be constructed at a particular size, such as at a nano scale of magnitude, to enhance the surface area available for cell attachment and reactivity. In one embodiment, the bone graft material includes at least one nanofiber.

One factor influencing the mechanism of a dynamic scaffold 10 is the incorporation of relatively small diameter fibers 15 and the resulting implant 20. Porous, fibrous scaffolds 10 may be made by a variety of methods resulting in an interlocking, entangled, orientated three-dimensional fiber implant 20.

As illustrated in FIGS. 1A and 1B, these fibers 15 are not necessarily continuous, but may be short and discrete, or some combination of long, continuous fibers 15 and short, discrete fibers 15. The fibers 15 touch to define intersections 17 and also define pores or voids 37. By varying the fiber dimensions and interaction modes, the porosity of the resulting implant, as well as its pore size distribution, may be controlled. This enables control of total porosity of the implant (up to about 95% or even higher) as well as control of pore size and distribution, allowing for materials made with predetermined nano-(pore diameters less than about 1 micron and as small as 100 nanometers or even smaller), micro-(pore diameters between about 1 and about 10 microns), meso-(pore diameters between about 10 and about 100 microns), and macro-(pore diameters in excess of about 100 microns and as large as 1 mm or even larger) porosity. The pores 37 typically range in size from about 100 nanometers to about 1 mm, with the pore size and size distribution a function of the selected fiber size range and size distribution, as well as of the selected forming technique. However, it is understood that the fiber and pore size is not limited to these ranges, and while the description focuses on the nanofibers and nanopores, it is well understood that the bone graft material of the present disclosure may equally include macro sized fibers and pores to create range of diameters of fibers and pores.

An example of the effect of one distribution of pore size within an exemplary implant 20 and its volumetric contribution and surface area contribution is shown with reference to FIGS. 6A and 6B, which are further described below. The resulting implant or device 20 may thus be a nonwoven fabric made via a spunlaid or spun blown process, a melt blown process, a wet laid matt or 'glass tissue' process, or the like and may be formed to have the characteristics of a felt, a gauze, a cotton ball, cotton candy, or the like.

Typically, macro-, meso-, and microporosity occur simultaneously in the device 20 and, more typically, are interconnected. It is unnecessary here to excessively quantify each type of porosity, as those skilled in the art can easily characterize porosity using various techniques, such as mercury intrusion porosimetry, helium pycnometry, scanning electron microscopy and the like. While the presence of more than a handful of pores within the requisite size range is needed in order to characterize a device 20 as having a substantial degree of that particular type of porosity, no specific number or percentage is called for. Rather, a qualitative evaluation by one skilled in the art shall be used to determine macro-, meso-, micro-, and/or nanoporosity. In some embodiments, the overall porosity of the porous, fibrous implants 20 will be relatively high, as measured by pore volume and typically expressed as a percentage. Zero percent pore volume refers to a fully or theoretically dense material. In other words, a material with zero porosity has no pores at all. Likewise, one hundred percent pore volume would designate "all pores" or air. One skilled in the art will be versed in the concept of pore volume and will readily be able to calculate and apply it.

Bone graft implants 20 typically have pore volumes in excess of about 30%, and more typically may have pore volumes in excess of 50% or 60% may also be routinely attainable. In some embodiments, scaffolding implants 20 may have pore volumes of at least about 70%, while other embodiments may typically have pore volumes in excess of about 75% or even 80%. Bone graft implants may even be prepared having pore volumes greater than about 90%-97%.

It is advantageous for some bone graft implants 20 to have a porosity gradient that includes macro-, meso-, and microporosity, and in some cases nanoporosity. In other words, the implants 20 can possess a porosity gradient such that the size of the pores as well as the placement of the pores can vary throughout the implants 20. The combination of fibers and particulates to create the appropriate compression resistance and flexibility is retained when the bone graft implant 20 is wetted. Bone graft implants 20 are also typically characterized by interconnected porosity, as such is correlated with increased capillary action and wicking capability. Such bone graft implants 20 should be capable of rapidly wicking and retaining liquid materials for sustained release over time.

The fibers 15 typically have non-fused linkages 35 that provide subtle flexibility and movement of the scaffolding 10 in response to changes in its environment, such as physiological fluctuations, cellular pressure differences, hydrodynamics in a pulsatile healing environment, and the like. This in vivo environment can and will change over the course of the healing process, which may last as long as several months or even longer. The scaffold 10 typically retains its appropriate supportive characteristics and distribution of pores 37 throughout the healing process such that the healing mechanisms are not inhibited. During the healing process, the pores 37 defined by the matrix of interlocking and tangled fibers 15 may serve to carry biological fluids and bone-building materials to the site of the new bone growth. The fluids likewise slowly dissolve fibers 15 made of bioactive glass and the like, such that the scaffolding 10, and particularly the pores 37, changes in size and shape in dynamic response to the healing process.

Scaffolds 10 are typically provided with a sufficiently permeable three-dimensional microstructure for cells, small molecules, proteins, physiologic fluids, blood, bone marrow, oxygen and the like to flow throughout the entire volume of the scaffold 10. Additionally, the dynamic nature of the scaffold 10 grants it the ability to detect or respond to the microenvironment and adjust its structure 20 based on forces and pressure exerted elements within the microenvironment.

Additionally, scaffolds 10 typically have sufficient three-dimensional geometries for compliance of the bone graft implant or device 20 when physically placed into an irregular shaped defect, such as a void, hole, or tissue plane as are typically found in bone, tissue, or like physiological site. The devices 20 typically experience some degree of compaction upon insertion into the defect, while the permeable characteristics of the scaffolds 10 are maintained. Typically, as with the placement of any bone void filler, the device 20 remains within 2 mm of the native tissue in the defect wall.

Bone graft implants or devices 20 made from the scaffolding 10 can appear similar to felts, cotton balls, textile fabrics, gauze and the like. These forms have the ability to wick, attach and contain fluids, proteins, bone marrow aspirate, cells, as well as to retain these entities in a significant volume, though not necessarily all in entirety; for example, if compressed, some fluid may be expulsed from the structure.

Another advantage of the bone graft implants or devices 20 is their ability to modify or blend the dynamic fiber scaffolds 10 with a variety of carriers or modifiers to improve handling, injectability, placement, minimally invasive injection, site conformity and retention, and the like while retaining an equivalent of the 'parent' microstructure. Such carriers ideally modify the macro-scale handling characteristic of the device 20 while preserving the micro-scale (typically on the order of less than 100 micrometers) structure of the scaffolding 10. These carriers resorb rapidly (typically in less than about 2 weeks; more typically in less than about 2 days) without substantially altering the form, microstructure, chemistry, and/or bioactivity properties of the scaffolding. These carriers include polaxamer, glycerol, alkaline oxide copolymers, bone marrow aspirate, and the like.

Figure 2A:
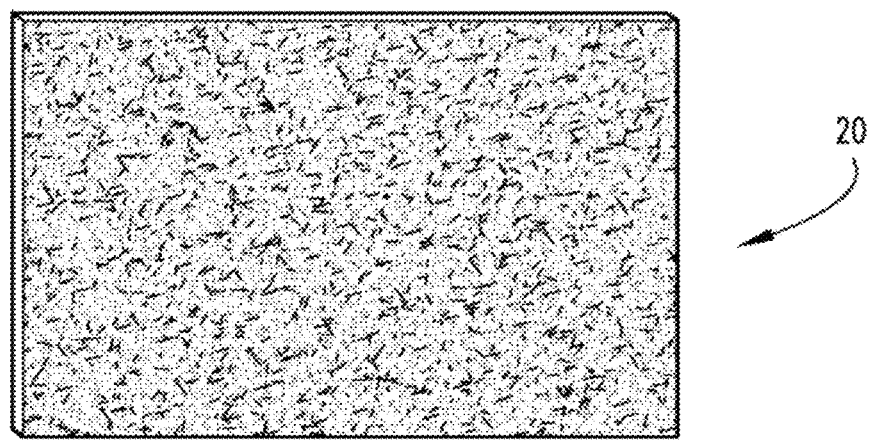
FIG. 2A is a perspective view of a first interlocking, entangled porous construct formed of the fibrous bioactive glass matrix of FIG. 1.
Figure 2B:
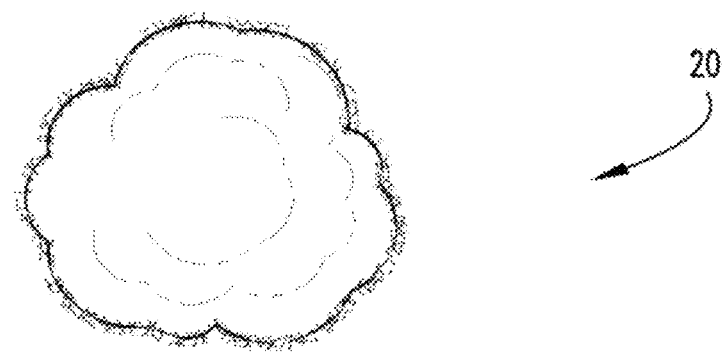
FIG. 2B is a perspective view of a second interlocking, entangled porous construct formed of the fibrous bioactive glass matrix of FIG. 1.

FIG. 2A shows an embodiment of an implant 20 in the form of a strip or sheet, for example. FIG. 2B shows an embodiment of an implant 20 in the form of a three-dimensional structure similar to a cotton ball, for example. In one example, a plurality of interlocking fibers 15 are spun or blown into a randomly oriented assemblage 20 having the general appearance of a cotton ball. The fibers 15 are typically characterized as having diameters of from less than about 1000 nm (1 micrometer) ranging up to approximately 10,000 nm (10 micrometers). The resulting cotton-ball device 20 may be formed with an uncompressed diameter of typically from between about 1 and about 6 centimeters, although any convenient size may be formed, and may be compressible down to between about ½ and ¼ of its initial size. In some cases, the device 20 can substantially return to its original size and shape once the compressive forces are removed (unless it is wetted with fluids, which kind of locks the device into desired shape and density, or is vacuum compressed). However, in many cases the device 20 may remain deformed. By varying the relative diameters of some of the fibers 15, structures ranging from 'cotton ball' to 'cotton candy' may be produced, with varying ranges of fiber diameters from less than about 10 nm to greater than about 10 microns.

Figure 2C:
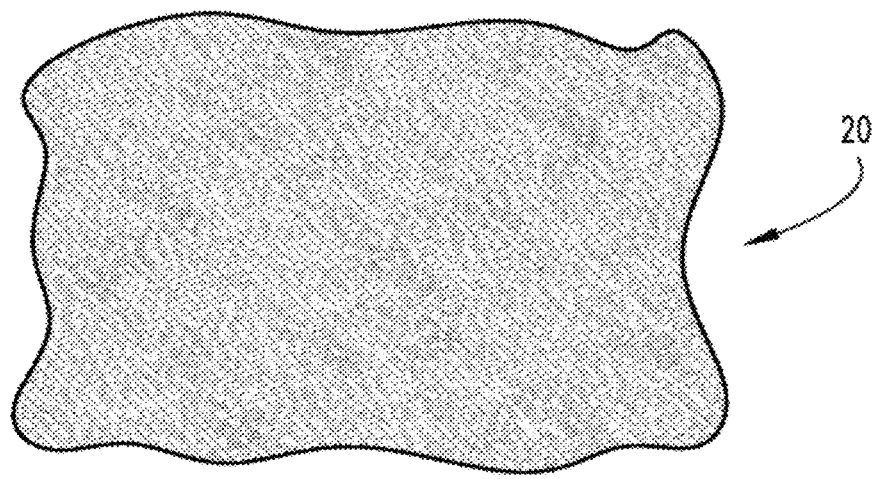
FIG. 2C is a perspective view of a third interlocking, entangled porous construct formed of the fibrous bioactive glass matrix of FIG. 1.

FIG. 2C shows an embodiment of the implant 20 in the form of a woven mesh or fabric, for example. In one example, fibers 15 may be woven, knitted, or otherwise formed into a fabric device 20 having a gauze-like consistency. The fibers 15 are typically greater than 1 about micrometer in diameters and may be as large as about 100 micrometers in diameter. The micro-scale orientation of the fibers 15 is typically random, although the fibers may be somewhat or completely ordered. On a macro-scale, the fibers 15 are typically more ordered. The constituency of these devices 20 may have varying amounts of smaller fibers 15 incorporated therein to maintain the self-constrained effect.

Figure 3A:
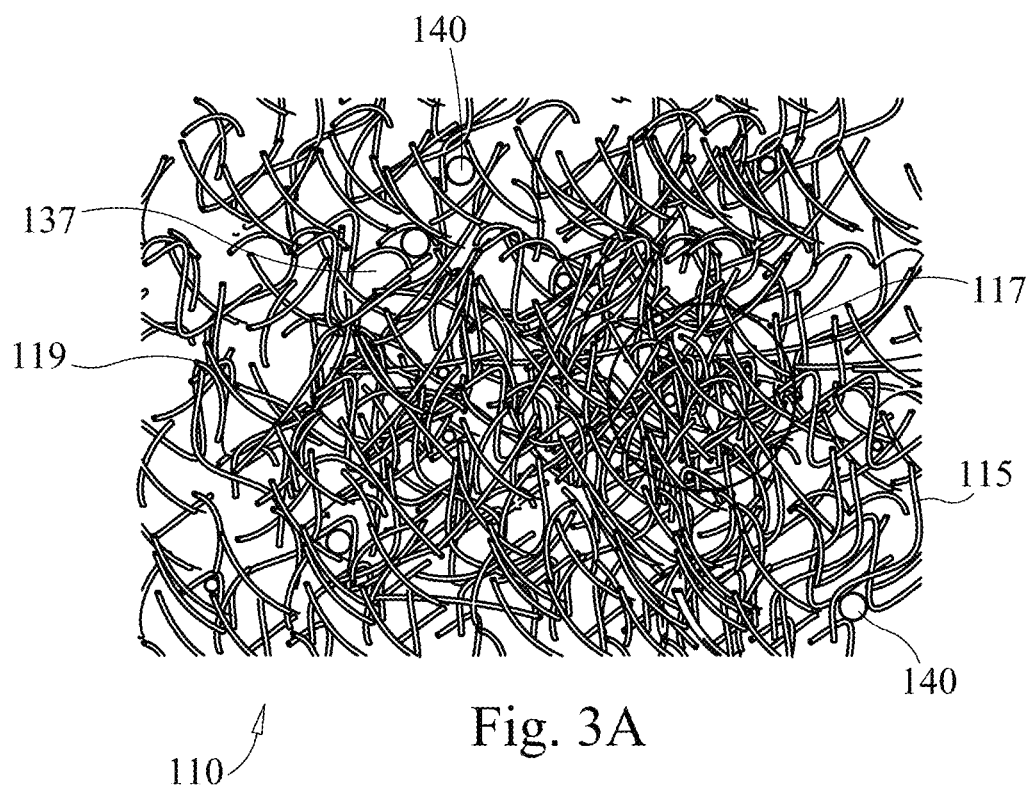
FIG. 3A is an illustration of a dynamic bioactive glass matrix having both fibers and particulate according to another embodiment of the present disclosure.
Figure 3B:
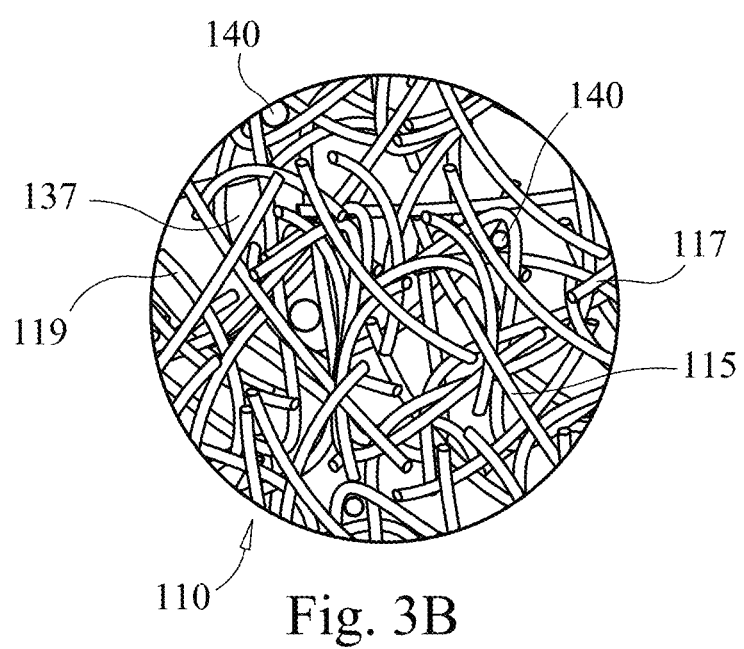
FIG. 3B is an enlarged view of the matrix of FIG. 3A.

FIGS. 3A and 3B illustrate another embodiment of the present disclosure, a bioactive fibrous scaffold 110 as described above with respect to FIGS. 1A and 1B, but having glass microspheres or particulate 140 distributed therethrough. The glass particulate 140 is typically made of the same general composition as the fibers 115, but may alternately be made of other, different compositions. One advantage of the presence of particulate 140 in the implant 120 is its contribution to the implant's 120 overall compression resistance. Since one function of the implant 120 is typically to absorb and retain nutrient fluids that feed the regrowth of bone, it is advantageous for the implant to offer some level of resistance to compressive forces, such that the liquids are not prematurely 'squeezed out'. Particulate 140, whether spherical or particulate, stiffens the implant, which is otherwise a porous scaffolding primarily composed of intertangled fibers 115. The particulate 140 can act as pillars, lending structural support to the overall implant 120.

The glass particulate 140 is typically generally spherical, but may have other regular or irregular shapes. The glass particulate 140 typically varies in size, having diameters ranging from roughly the width of the fibers 115 (more typically, the struts 119) to diameters orders of magnitude greater than the typical fiber widths. Particulate 140 may also vary in shape, from generally spherical to spheroidal, or elliptical to irregular shapes, as desired. The particulate 140 may even be formed as generally flat platelets; further, the platelets (or other shapes) may be formed having perforations or internal voids, to increase the effective surface area and dissolution rate. Likewise, the shape of the particulate 140 may be varied to influence such factors as bone cell attachment, particulate coatability, and the like.

In one embodiment, the glass particulates 140 may have an average diameter of about 20 microns to about 1 millimeter. In another embodiment, the particulates 140 may have an average diameter of about 300 to 500 microns. In still another embodiment, the glass particulates 140 may have an average diameter of about 350 microns.

As with the fibers, bioactive glass particulate 140 may be coated with organic acids (such as formic acid, hyaluronic acid, or the like), mineralogical calcium sources (such as tricalcium phosphate, hydroxyapatite, calcium sulfate, or the like), antimicrobials, antivirals, vitamins, x-ray opacifiers, or other such materials. While smaller particulate may tend to lodge in or around fiber intersections 117, larger particulate tend to become embedded in the scaffolding 120 itself and held in place by webs of fibers 115. Pore-sized microspheres may tend to lodge in pores 137.

The glass particulate 140 may be composed of a predetermined bioactive material and tailored to dissolve over a predetermined period of time when the scaffolding 110 is placed in vitro, so as to release a predetermined selection of minerals, bone growth media, and the like at a predetermined rate. The composition, size and shape of the glass particulate 140 may be varied to tailor the resorption rate of the bioactive glass, and thus the rate at which minerals and the like are introduced into the body (and likewise, how long the particulate 140 is available to provide increased compression resistance to the scaffolding implant 20). For example, for a given bioactive glass composition and particulate volume, irregularly shaped particulate 140 would have more surface area than spherical particulate 140, and would thus dissolve more rapidly.

Further, the glass particulate 140 may be hollow bioactive glass, polymer or the like microspheres filled with specific mixture of medicines, antibiotics, antivirals, vitamins or the like to be released at and around the bone regrowth site at a predetermined rate and for a predetermined length of time. The release rate and duration of release may be functions of particulate size, porosity and wall thickness as well as the distribution function of the same.

Figure 4A:
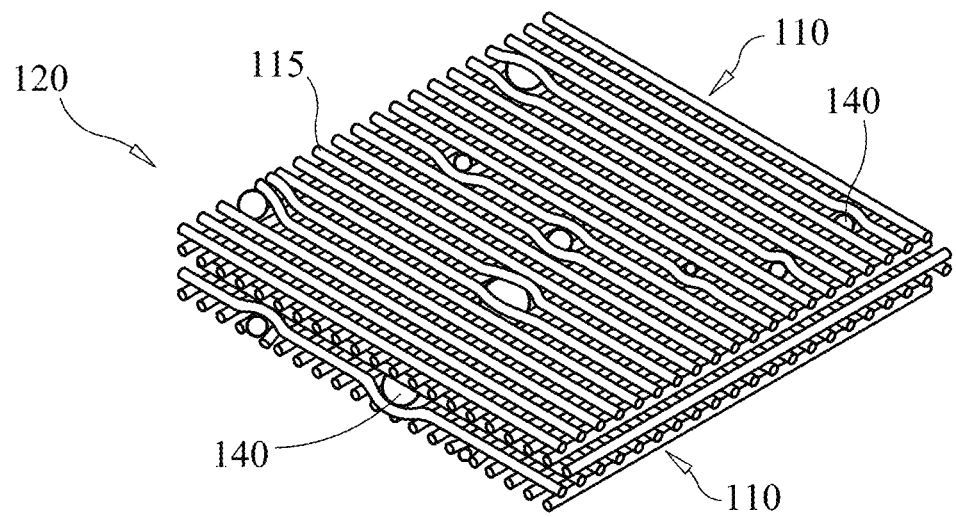
FIG. 4A is an illustration of an exemplary bioactive glass fiber bone graft material according to the present disclosure having an organized parallel fiber arrangement with descending layers of fibers in cross-directional relationship to alternating layers of fibers.
Figure 4B:
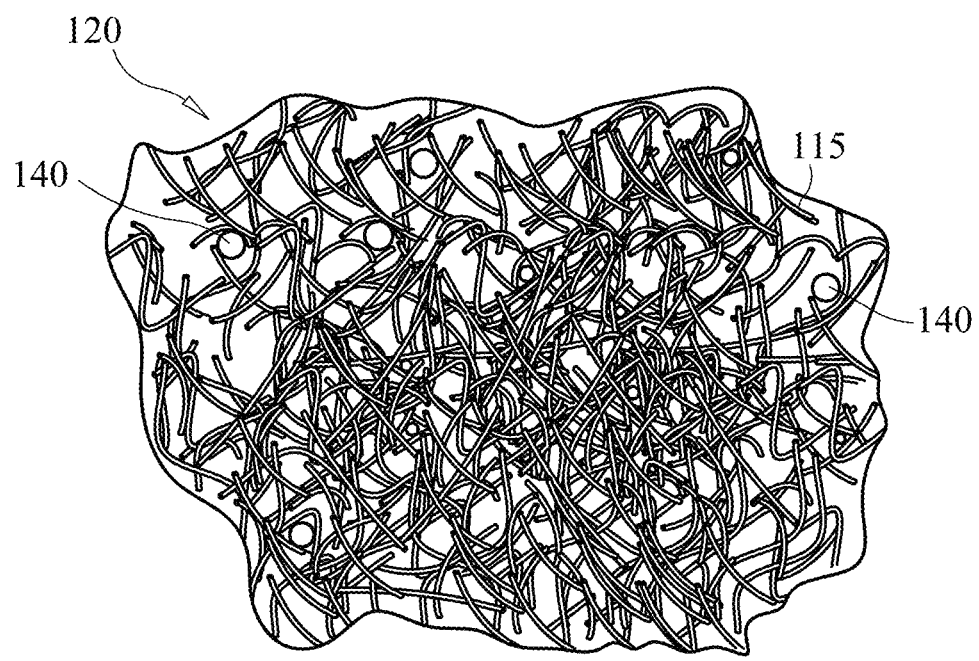
FIG. 4B is an illustration of an exemplary bioactive glass fiber bone graft material in a randomly arranged spun-glass structure with bioactive glass particulate.
Figure 4C:
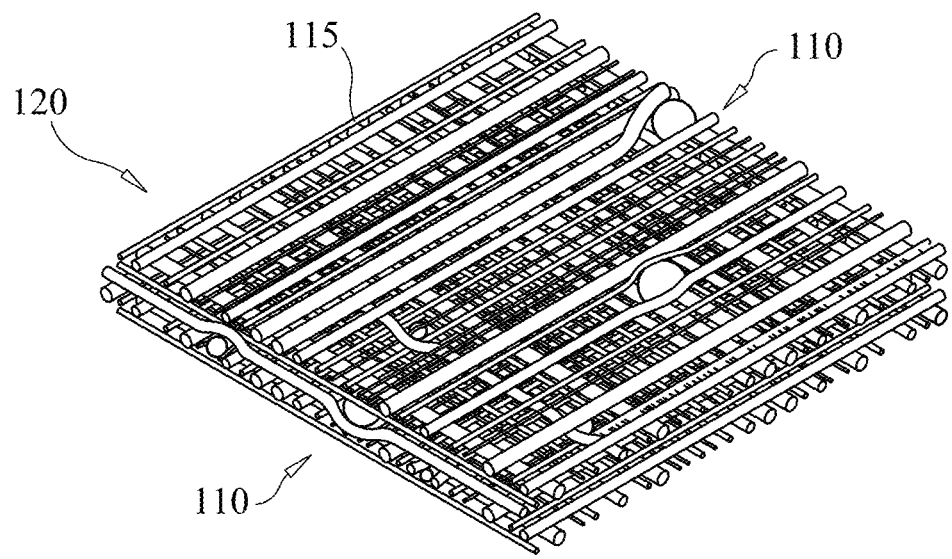
FIG. 4C is an illustration of an exemplary bioactive glass fiber bone graft material constructed as a mesh with descending layers of fibers being arranged so as to have a different degree of porosity relative to the previous layer of fibers, thus providing a cell filter functionality.

As discussed above, the shape and texture of the bone graft material may be randomly configured to maximize its overall volume, surface area, and pliability or, in stark contrast, can be manufactured with the bioactive glass fibers in a more rigid and uniform arrangement, such as, for example in a mesh or matrix type assembly. In a mesh or matrix assembly, as illustrated by the non-limiting examples shown in FIGS. 4A to 4C, the glass fibers can be arranged in a stacked arrangement limiting the flexibility in a directional manner, or, the fibers can be layered wherein alternating layers are in a crossed relationship one to the other. In FIG. 4A, the matrix assembly 110 is shown having an ordered configuration with discrete layers comprising fibers 115 and particulate 140. In FIG. 4B, the matrix assembly is shown having a randomly arranged configuration of fibers 115 and particulate 140 dispersed throughout. In FIG. 4C, the matrix assembly 110 is shown having a configuration in which the layers have different porosities due to differences in the spacing of the fibers 115 and particulate 140 throughout each layer. That is, the size of the pores 137 varies throughout the matrix assembly due to the unevenly spaced fibers 115 and particulate 140. It should be understood that, while FIGS. 4A and 4C show discretely aligned fibers 115 for the purposes of illustrating the concept herein, the individual layers of material 110 may include fibers 115 and particulate 140 that are unorganized and randomly aligned.

An advantage of the present disclosure is the wide variety of alternative configurations and structural arrangements that result in an equally varied functionality of the material being used by a surgeon. As illustrated in FIGS. 4A-C, the bone graft material of the present disclosure can include embedded bioactive glass particles within the bioactive glass fiber construct. The inclusion of such particles, as determined by the quantity, size, and characteristics of the particles, can affect the compressibility, bioabsorbability, and porosity of the resulting bone graft material. Additional additives, such as calcium phosphates (CaP), calcium sulfates (CaS), hydroxyapatite (HA), carboxymethycellulose (CMC), collagen, glycerol, gelatin, and the like can also be included in any of the many varied constructions of the bioactive glass fiber bone graft material to assist in bone generation and patient recovery. Such additives may be in the range of 0 to 90 percent porous. Another additive, collagen, may be included and may also be of the ultraporous kind having a porosity of up to 98 percent.

In one embodiment, the surface area of the bone graft material is maximized to increase the bone ingrowth into the structural matrix of the material. Another useful variable is the capability of the bone graft material to selectively be composed and configured to provide layers of varying porosity, such as nano-, micro-, meso-, and microporosity, so as to act as a cell filter controlling the depth of penetration of selected cells into the material. Because the preparation of the bone graft material can be selectively varied to include bioactive glass fibers and/or particles having different cross-sectional diameters, shapes and/or compositions, the material properties may be tailored to produce a bone graft material with differential absorption capabilities. This feature permits the surgeon to select a bone graft material specifically for the needs of a specific situation or patient. Controlling the pace of bone ingrowth into the bioactive glass matrix of the material allows the surgeon to exercise almost unlimited flexibility in selecting the appropriate bone graft material for an individual patient's specific needs.

In another embodiment, the bioactive glass was formulated with strontium partially replacing calcium. The partial replacement of calcium with strontium yields a bioactive glass with a reduced resorption/reaction rate and also with an increased radiodensity or radioopacity. Thus, the bioactive glass stays present in the body for a longer period of time and also presents a more readily visible x-ray target.

In another embodiment, silver (or other antimicrobial materials) may be incorporated into the bioactive glass fiber scaffolding structural matrix. Silver is an antimicrobial material, and enhances the inherent antimicrobial properties of the bioactive glass material. Typically, silver is added as a dopant to very fine bioactive glass fibers, such that the silver is quickly released as the very fine fibers dissolve at the implant site, allowing the silver to act as an antimicrobial agent to prevent infection immediately after surgery while the remaining scaffolding material does its work. Alternately, Ag may be introduced as fibers and interwoven with the bioactive glass fibers, as particles similar to the glass particulate discussed above, or the like. Of course, varying the composition of the bioactive glass from which the fibers are formed to create an alkaline (high pH in the range of 8-10) glass may also provide the material with antimicrobial properties.

One advantage of the current invention is that it is dynamic, and can be easily molded into various shapes or form, without losing the essential structure and porosity. By packaging the material in a functional tray, where the tray acts as a mold, the material can be provided in various shapes in the operating room. Especially, the material becomes a cohesive mass when a fluid such as blood, saline, bone marrow, other natural body fluids, etc. is added.

Figure 5A:
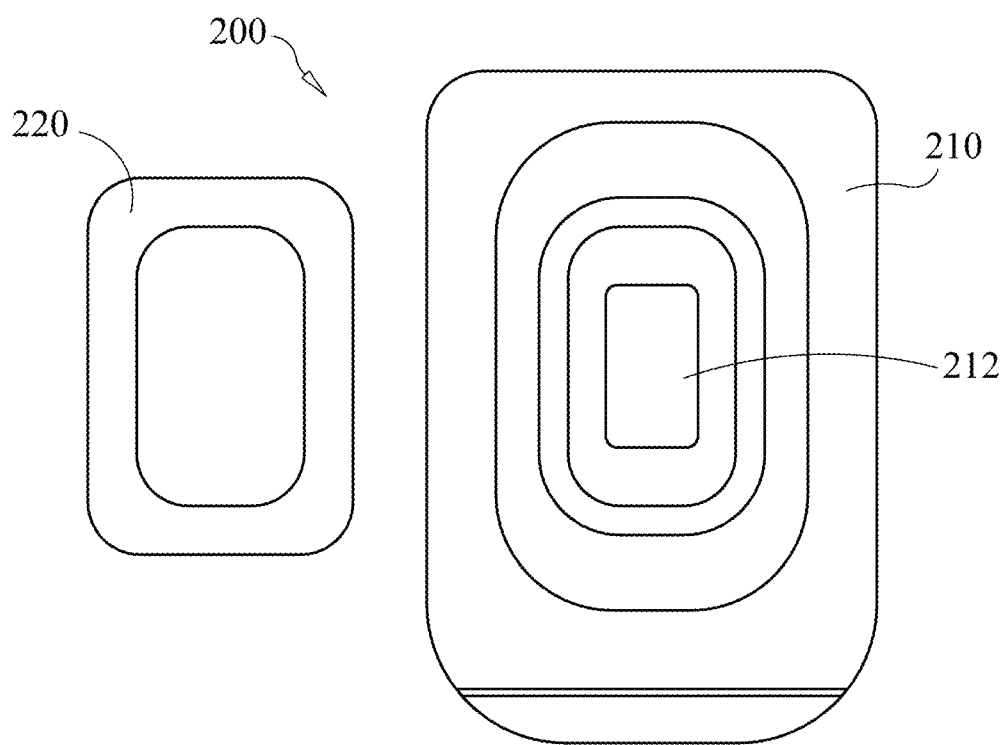
FIG. 5A is a perspective view of a packaging container according to a medical kit embodiment of the present disclosure.
Figure 5B:
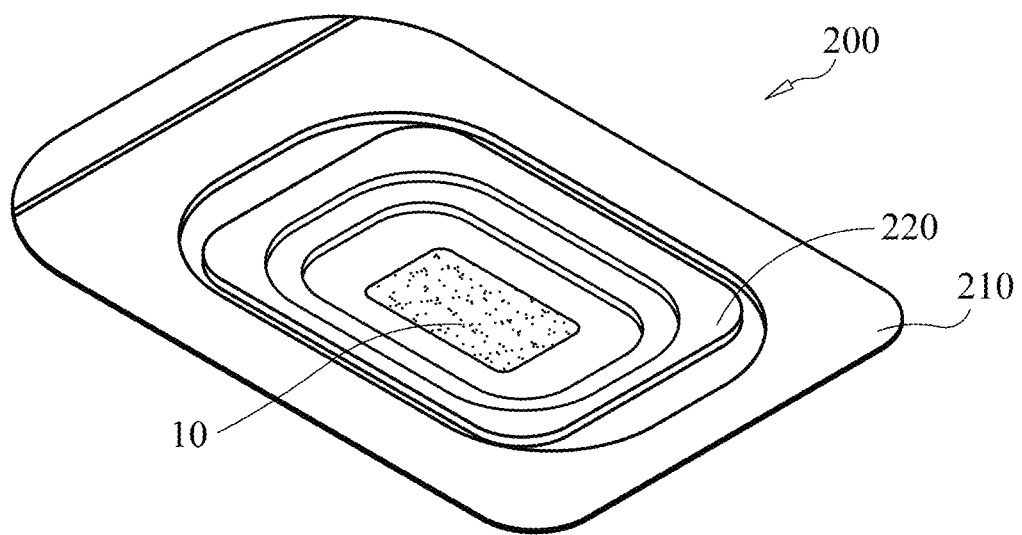
FIG. 5B is a perspective view of the embodiment of FIG. 5A including fibrous bioactive bone graft material positioned in the kit.
Figure 5C:
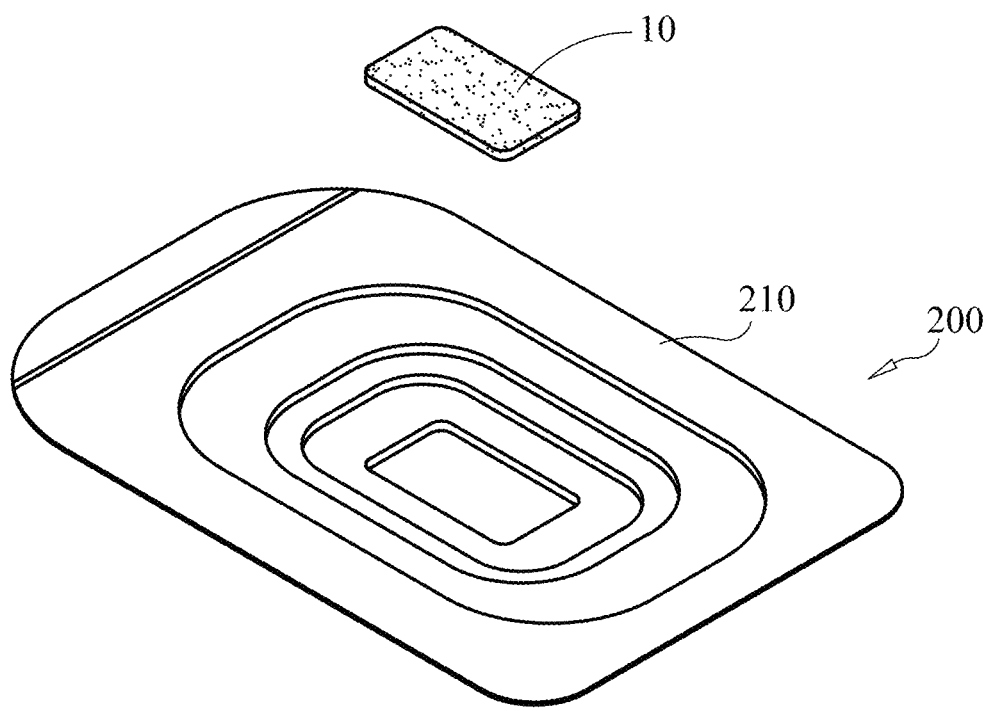
FIG. 5C is a perspective view of the bone graft material of FIG. 5B removed from the kit.

In an embodiment, as shown in FIGS. 5A to 5C, the bone graft material is provided as part of a surgical kit 200. The kit 200 includes a tray portion 210 having a recess or well 212, and more typically a set of nested recesses, for storing, holding and manipulating the bone graft material 10, 110, and a lid portion 220 for sealingly engaging the tray portion 210. The tray and lid portions 210, 220 are typically formed from thermoplastic materials, but may alternately be made of any convenient materials.

The deepest recess chamber 212 typically has a simple geometry, such as a rectangular block or wedge shape, such that the so-loaded bone graft material likewise has a simple geometry. Other geometries are described in a co-pending and commonly owned U.S. patent application Ser. No. 12/914,376, entitled "DYNAMIC BIOACTIVE BONE GRAFT MATERIAL AND METHODS FOR HANDLING," filed Oct. 28, 2010, the disclosure of which is hereby incorporated by reference.

The bone graft material 10, 110 is typically provided as an intertangled or interwoven mass of bioactive glass fibers. The bioactive glass fibers may be provided in format that is ready to be surgically emplaced in a bony cavity (such as a woven or mesh format), or may be provided in a format that requires additional preparation prior to emplacement (such as a more loosely intertangled format) that requires the addition of a liquid, such as saline, glycerol, gelatin, plasma, or collagen gel or chips, to assist in rendering the mass of bioactive glass more pliable and structurally unitary. Such liquids may optionally be included in the kit packaging 200, or provided separately.

In one example, a kit 200 is provided, including a tray body 210 and a lid 220 engagable with the tray body. The tray body 210 includes one or more recesses 212 for containing a volume of bioactive glass fibers 10. The volume of bioactive glass fibers may be woven, knitted, intertangled or provided as a loose stack. The volume of bioactive glass fibers may optionally include fibers of other compositions, such as antimicrobial silver, polymers, or alternate glass compositions, and may also optionally include particulate matter or particulate of the same bioactive glass composition, or alternate compositions such as alternate glass, metal, metal oxide, medicinal, nutritive, and/or antimicrobial or the like. The kit may also optionally include a liquid, such as saline or collagen gel, for mixing with the bioactive glass volume.

In operation, the surgeon removes the lid 220 of the kit 200 and removes a portion of the included bioactive glass material 10. The bioactive glass material may then be shaped and sized by the surgeon for insertion into a bony cavity. This process may involve the addition of an appropriate liquid to the bioactive glass material, such as saline, collagen gel, plasma, blood, or the like, to achieve a desired degree of pliability and/or structural integrity. Once the bioactive glass material is sized and shaped as desired, it is inserted into the bony cavity. This process may be done as a single operation or as a series of steps.

Figures 6A, 6B:
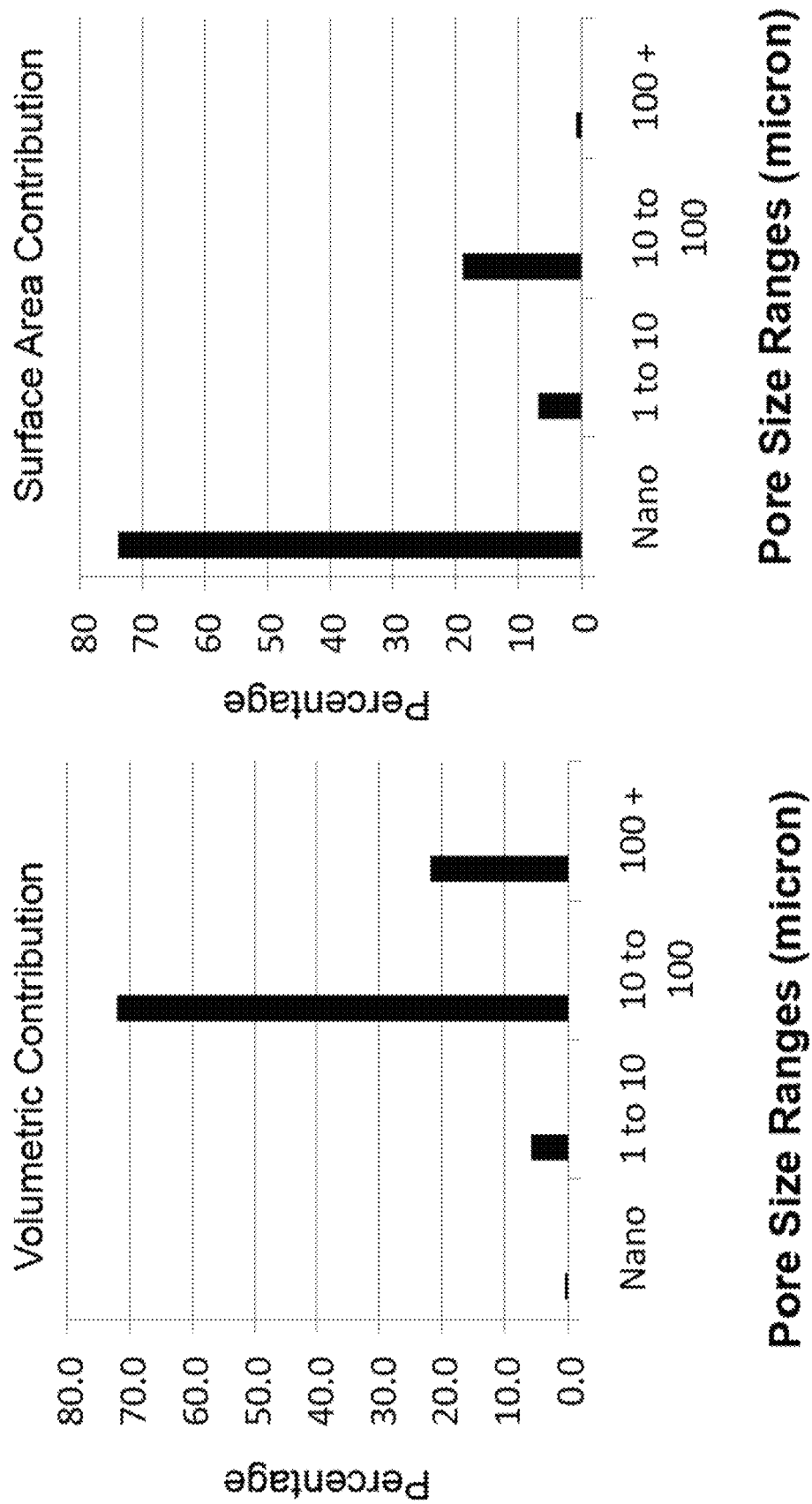
FIG. 6A graphically shows volumetric contribution of an embodiment of the bone graft material based on its pore size distribution.
FIG. 6B graphically shows surface area contribution of an embodiment of the bone graft material based on its pore size distribution.

FIGS. 6A and 6B illustrate graphically volumetric contribution and surface area contribution of an embodiment of the bone graft material based on its pore size distribution. As noted, in one embodiment, the bone graft material of an implant 20 may have a structure having varying porosity, such as nano-, micro-, meso-, and macro-porosity. As shown in FIGS. 6A and 6B, although the mesopores and micropores contribute to a large portion of the volume of the bone graft material, the nanopores contribute a significantly large portion of the surface area provided by the bone graft material. That is, for a give volume, the embodiments may utilize a porosity distribution that includes nanopores to obtain a higher surface higher for a given volume. Of course, these and other features and advantages can be provided by the embodiments.

Figure 7:
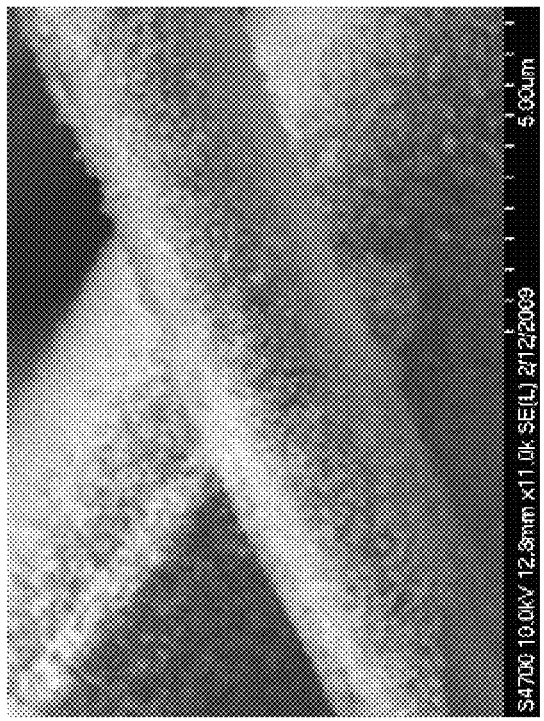
FIG. 7 shows time lapse photomicrographs of fibers of an embodiment of the present disclosure after one day and three days.
Figure 7:
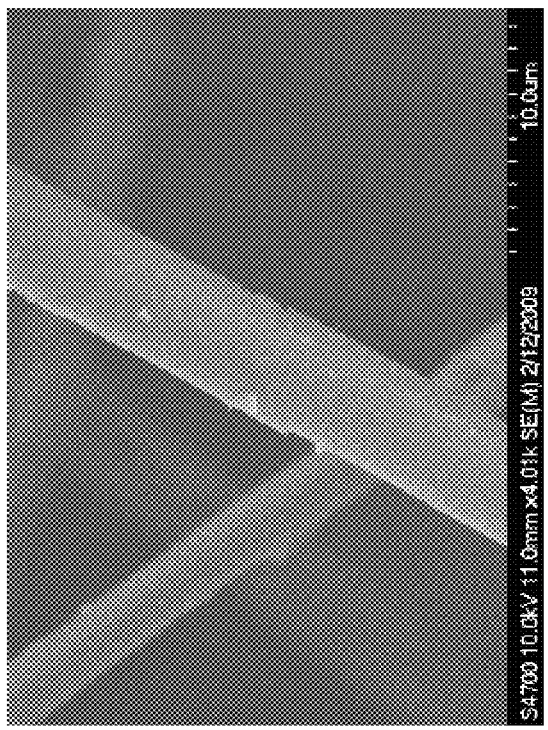
Figure 8:
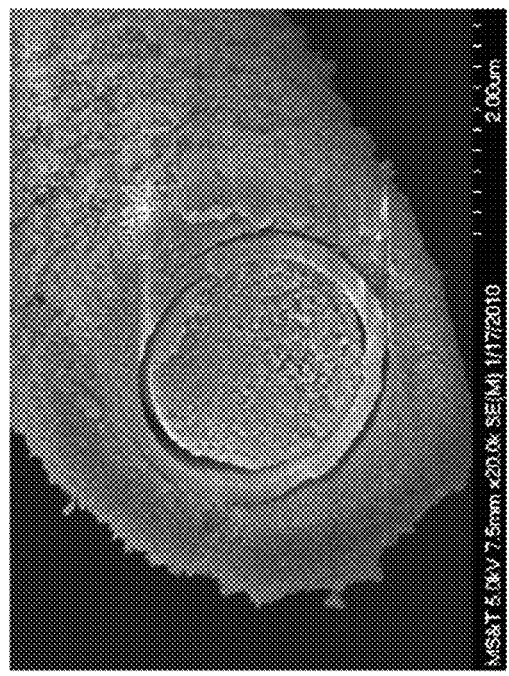
FIG. 8 shows time lapse photomicrographs of fibers of an embodiment of the present disclosure after three days.
Figure 8:
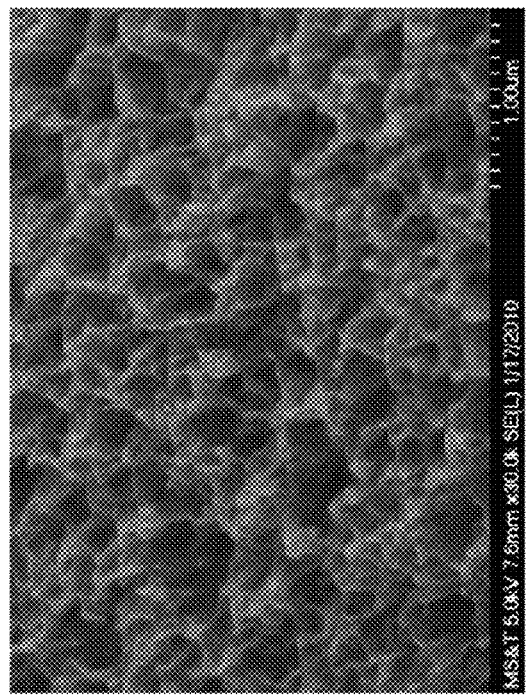

FIG. 7 shows time lapse photomicrographs of fibers of an embodiment of the present disclosure immersed in simulated body fluid at 37° C. after one day and three days, while FIG. 8 shows time lapse photomicrographs of fibers of an embodiment of the present disclosure immersed in simulated body fluid at 37° C. after three days.

Figure 9:
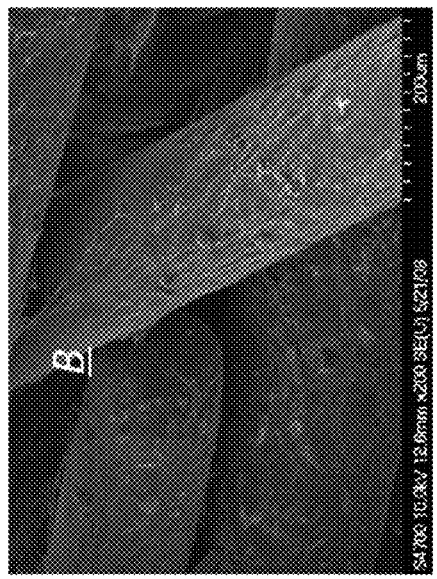
FIG. 9 shows a series of time lapse photomicrographs showing cell growth properties of fibers of an embodiment of the present disclosure at various time intervals.
Figure 9:
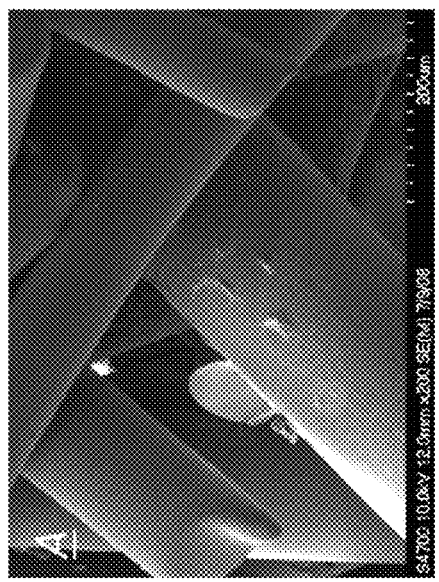
Figure 9:
Figure 10:
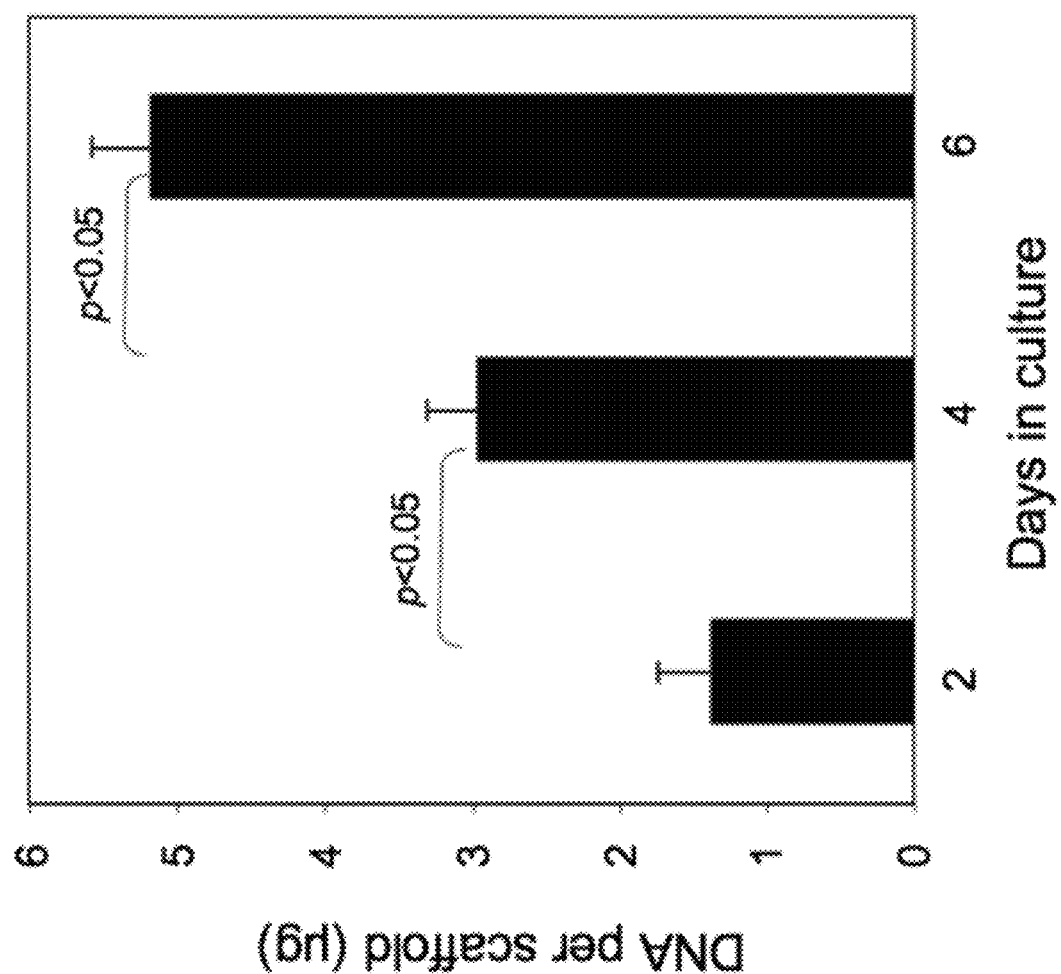
FIG. 10 shows a graph of osteoblast cell growth exhibited during testing of fibers of an embodiment of the present disclosure at various time intervals.
Figure 11:
FIG. 11 shows a photomicrograph of a fiber that has been seeded with mesenchymal stem cells.

FIG. 9 shows a series of time lapse scanning electron micrographs (SEMs) showing osteoblast cells cultured on glass fiber scaffolds of the present disclosure for 2, 4 and 6 days. As shown, there is increased cell density during the 6-day incubation. FIG. 10 shows a graph of osteoblast cell growth exhibited on the glass fiber scaffold of FIG. 9 for 2, 4 and 6 days with an initial seeding of 100,000 MC3T3-E1 cells per scaffold. FIG. 11 shows a photomicrograph of a fiber that has been seeded with mesenchymal stem cells. Such cells may assist with the osteostimulative effect of osteoblast proliferation and differentiation. The effect can be measured based on determining DNA content and elevated presence of osteocalcin and alkaline phosphatase levels.

Comparative Animal Study

Figure 12:
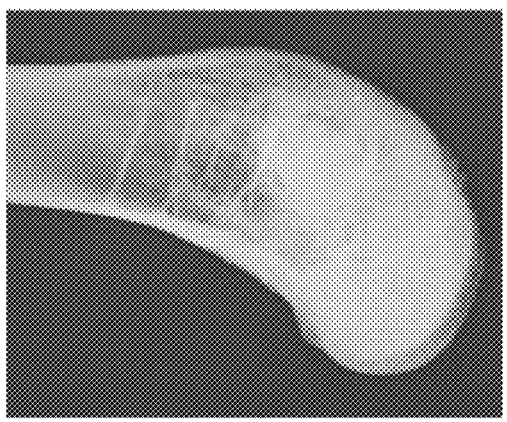
FIG. 12 shows a series of radiographic images from testing performed on a mammal comparing the performance of an embodiment of the bone graft material with another material at various time intervals.
Figure 12:
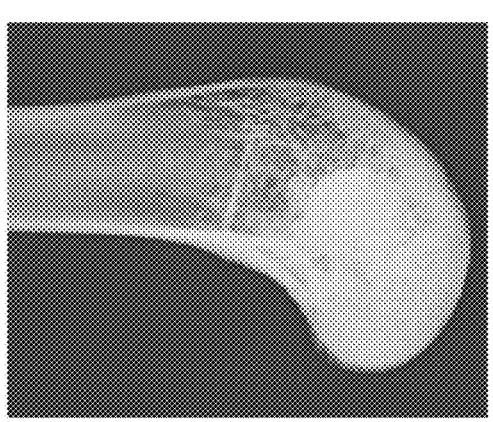
Figure 12:
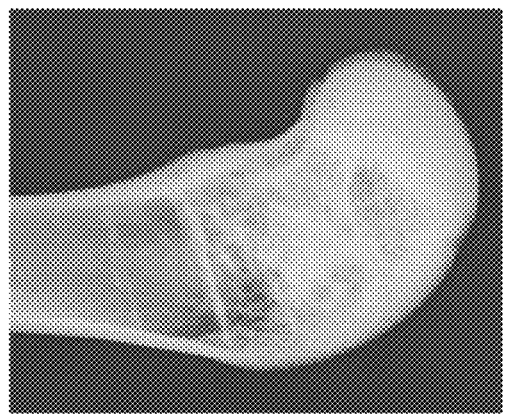
Figure 12:
Figure 12:
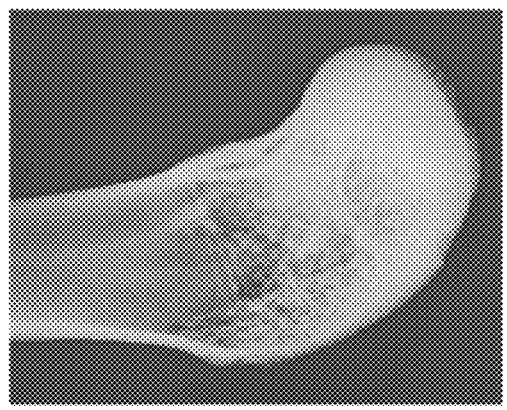
Figure 12:
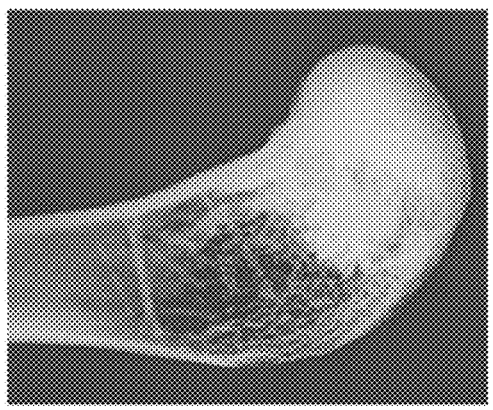
Figure 13:
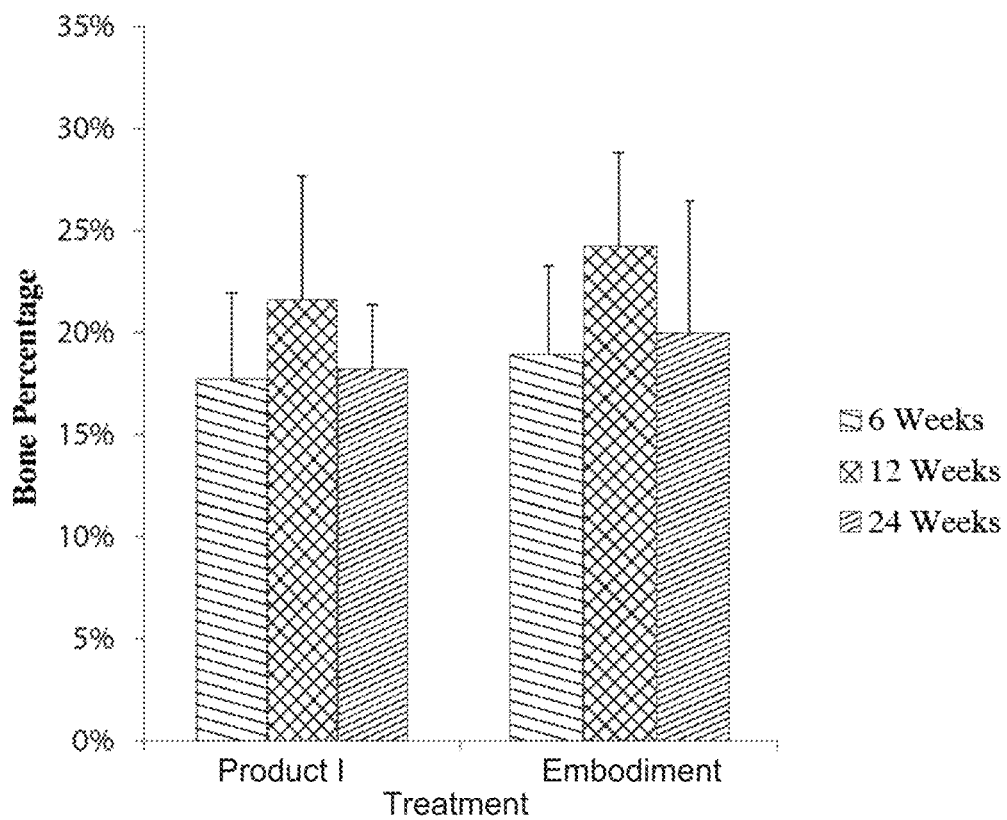
FIG. 13 shows a graphical comparison of new bone growth exhibited by the embodiment of the bone graft material with the other material of FIG. 12 at various time intervals.
Figure 14:
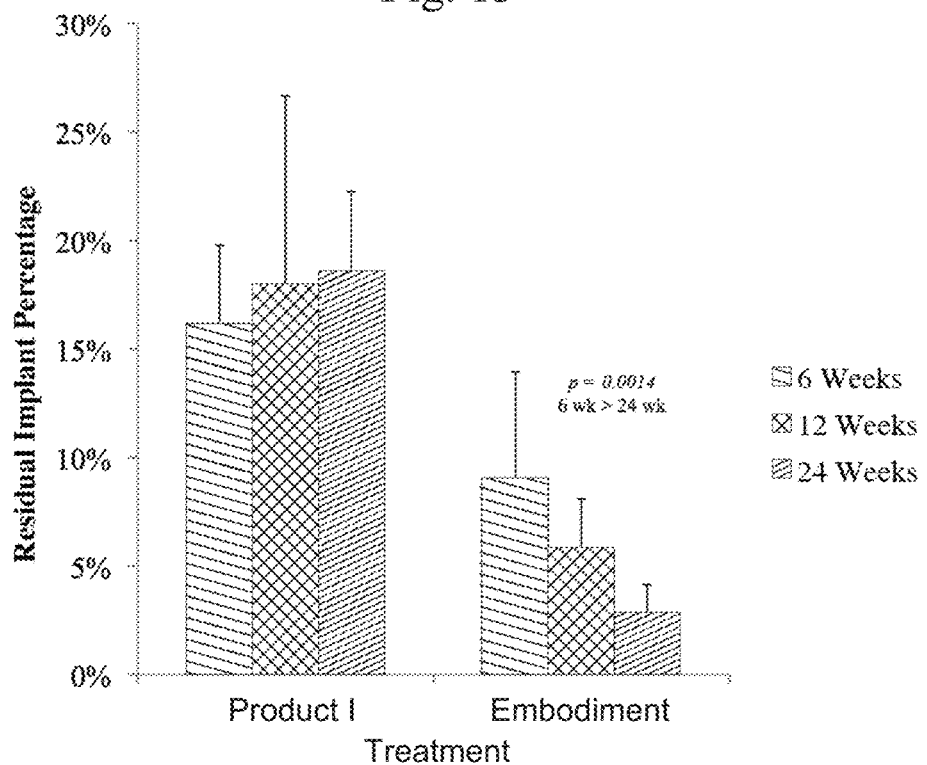
FIG. 14 shows a graphical comparison of residual material remaining over time by the embodiment of the bone graft material with the other material of FIG. 12 at various time intervals.

FIGS. 12-14 show some results of testing of an embodiment of the fibrous bone graft material of the present disclosure on a mammal (specifically, in this case a rabbit.) In the testing, a bilateral distal femoral bone defect was created having a size of approximately 5 mm in diameter and 10 mm in length. In addition to an embodiment of the bone graft material of the disclosure, the testing was performed along with a commercially available bone graft substitute, Product #1, in this comparison study. Product #1 is a silicate substituted bone graft material (ACTIFUSE™ available from ApaTech, Inc. of Foxborough, Mass.) During the study, it was observed that the bone graft material of the present disclosure solicits a more dynamic bone growth response than with traditional synthetic bone graft materials, and leads to more physiologic bone healing and remodeling. At 6 months, the majority of the base material was resorbed with evidence of bone remodeling at the surgical site. Further, the bone tissue appeared to integrate with surrounding bone.

From this study, FIG. 12 shows a series of radiographic images from testing performed comparing the performance of an embodiment the bone graft material with Product 1 at 6 weeks, 12 weeks and 24 weeks.

FIG. 13 shows a graphical comparison of percentage of new bone present after 6 weeks, 12 weeks and 24 weeks in the embodiment of the bone graft material with Product 1 during the comparative study.

FIG. 14 shows a graphical comparison of percentage of residual material remaining after 6 weeks, 12 weeks and 24 weeks in the embodiment of the bone graft material with Product 1 during the comparative study.

Table I. below shows the average ultimate compressive strength (ibf) and average ultimate compressive stress (psi) at 6 weeks, 12 weeks and 24 weeks for the embodiment of the fibrous material of the present disclosure and Product 1, compared with native, unoperated bone. As can be seen, the embodiment of the bone graft material tested shows much more similar mechanical properties to native bone than does Product 1.

TABLE I

Mechanical Test Results

| Specimen | Timepoint | Average Ultimate Compressive Strength (ibf) | Average Ultimate Compressive Stress (psi) |
| --- | --- | --- | --- |
| Bone Graft Embodiment | 6 weeks | 17.3 ± 7.11 | 482.31 ± 254.29 |
| | 12 weeks | 26.84 ± 7.18 | 721.26 ± 145.18 |
| | 24 weeks | 12.8 ± 9.63 | 351.43 ± 266.09 |
| Product 1 | 6 weeks | 26.26 ± 13.04 | 731.26 ± 426.51 |
| | 12 weeks | 31.55 ± 25.34 | 855.15 ± 541.39 |
| | 24 weeks | 28.57 ± 21.77 | 855.15 ± 617.33 |
| Native Bone | | 14.75 ± 12.23 | 476.93 ± 407.54 |

Further, in histology evaluations at 6, 12 and 24 weeks, new bone growth appeared more normal in the bone graft embodiment than with Product 1. For example, even when the total amount of new bone growth was the same for both the bone graft embodiment and Product 1, the quality of the growth differed. In the bone graft embodiment, the microfibers were fully resorbed and replaced by normal healthy bone that had started to remodel to adapt to physiologic loading. The bone graft embodiment also displayed uniform and well distributed cell growth throughout. Product 1 showed localized growth similar to bone deposition. At 24 weeks or 6 months, the bone deposition of Product 1 appeared to have broken down into fibrous tissue growth. Conversely, at 24 weeks or 6 months, almost all of the remaining fibers of the bone graft embodiment were coated with new cells, and there was evidence of new vasculature formed. In other words, the normal architecture of healthy bone has already appeared in the bone graft embodiment. Thus, the histology images support the bone remodeling that is believed to have occurred already at this stage.

Although the bone graft material of the present disclosure is described for use in bone grafting, it is contemplated that the graft material of the present disclosure may also be applied to soft tissue or cartilage repair as well. Accordingly, the application of the fibrous graft material provided herein may include many different medical uses, and especially where new connective tissue formation is desired.

While the present disclosure has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a near infinite number of insubstantial changes and modifications to the above-described embodiments and that it would be impractical to attempt to describe all such embodiment variations in the present specification. Accordingly, it is understood that all changes and modifications that come within the spirit of the present disclosure are desired to be protected.

What is claimed is:

1. A method of treating a bone defect, comprising:
   providing a bone graft material, the material comprising:
   a porous matrix comprising a plurality of overlapping and interlocking bioactive glass fibers and bioactive glass particulates distributed throughout the fibers, the fibers and particulates each having varying diameters, and pores having a range of sizes defined by the spaces between said fibers and particulates, the varying diameters of the fibers and particulates controlling pore size and distribution of the range of pores and overall porosity of the matrix, the matrix further having a distributed porosity based on said range of sizes of the pores such that the matrix is configured for staged resorption, the pores comprising micropores and macropores;
   forming an implant from the bone graft material, the implant being formed by shaping the material into a shape and size for insertion into the bone defect; and
   implanting the formed implant into the bone defect.

2. The method of claim 1, wherein the pores further comprise nanopores or mesopores.

3. The method of claim 1, wherein the range of sizes of the pores is distributed based on a gradient across the matrix.

4. The method of claim 1, wherein the fibers are randomly oriented.

5. The method of claim 1, wherein the micropores range in diameter from about 1 micron to about 10 microns.

6. The method of claim 1, wherein the macropores range in diameter from about 100 microns to about 1 millimeter.

7. The method of claim 1, wherein the pores range in diameter from about 100 nanometers to about 1 millimeter.

8. The method of claim 1, wherein the matrix is configured with a porosity of at least 30%.

9. The method of claim 1, wherein the matrix is configured with a porosity of at least 95% prior to being shaped.

10. The method of claim 1, wherein the matrix is configured with a porosity of at least 80% after being shaped.

11. The method of claim 1, wherein the material further comprises a carrier material.

12. The method of claim 11, wherein the carrier material comprises collagen.

13. The method of claim 1, further having antimicrobial properties.

14. The method of claim 1, further including an additive comprising a tricalcium phosphate, calcium phosphate, calcium sulfate, carboxymethycellulose, collagen, hydroxyapatite, antimicrobial, antiviral, vitamin, x-ray opacifier, medicine, calcium, trace element, metal, metal oxide, nutrient, or acid.

15. The method of claim 1, further including an additive comprising silver, copper, strontium, magnesium or zinc.

16. The method of claim 1, further including an additive comprising an organic acid.

17. The method of claim 1, wherein the implant is shaped by molding the material in a mold tray.

18. The method of claim 1, wherein the material is compressible.

19. The method of claim 1, further including the step of adding a liquid to form a cohesive mass.

20. The method of claim 19, wherein the liquid comprises blood, saline, glycerin, gelatin, plasma, or bone marrow.

* * * * *